(12) United States Patent
Mohamed

(10) Patent No.: US 12,017,925 B2
(45) Date of Patent: *Jun. 25, 2024

(54) METHOD FOR TREATING POLLUTED COMPOSITION

(71) Applicant: Imam Abdulrahman Bin Faisal University, Dammam (SA)

(72) Inventor: Hanan Hussein Amin Mohamed, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/213,519

(22) Filed: Jun. 23, 2023

(65) Prior Publication Data
US 2023/0331581 A1    Oct. 19, 2023

Related U.S. Application Data

(63) Continuation of application No. 17/543,899, filed on Dec. 7, 2021, now Pat. No. 11,739,003, which is a
(Continued)

(51) Int. Cl.
*C01G 49/04* (2006.01)
*C30B 7/14* (2006.01)
(Continued)

(52) U.S. Cl.
CPC ............... *C01G 49/04* (2013.01); *C30B 7/14* (2013.01); *C30B 30/00* (2013.01); *B82Y 30/00* (2013.01);
(Continued)

(58) Field of Classification Search
CPC ............ C01G 49/04; C30B 7/14; C30B 30/00
See application file for complete search history.

(56) References Cited

U.S. PATENT DOCUMENTS

| | | |
|---|---|---|
| 11,235,983 B2 | 2/2022 | Mohamed |
| 2007/0086935 A1 | 4/2007 | Chen |
| 2013/0168228 A1 | 7/2013 | Ozin |

FOREIGN PATENT DOCUMENTS

| | | |
|---|---|---|
| CN | 104649329 B | 8/2016 |
| WO | 2009/140694 A2 | 11/2009 |

OTHER PUBLICATIONS

Ali, et al.; Green synthesis of α-Fe2O3 using Citrus reticulum peels extract and water decontamination from different organic pollutants; Energy Sources Part A: Recovery, Utilization, and Environmental Effects, vol. 39. No. 13; pp. 1425-1434; Sep. 8, 2017; 12 Pages.

(Continued)

*Primary Examiner* — James A Fiorito
(74) *Attorney, Agent, or Firm* — Oblon, McClelland, Maier & Neustadt, L.L.P.

(57) ABSTRACT

A method for producing crystalline α-$Fe_2O_3$ nanoparticles involving ultrasonic treatment of a solution of an iron (III)-containing precursor and an extract from the seeds of a plant in the family Linaceae. The method involves preparing an aqueous extract from the seeds of a plant in the family Linacae and dropwise addition of the extract to the solution of an iron (III)-containing precursor. The method yields crystalline nanoparticles of α-$Fe_2O_3$ having a spherical morphology with a diameter of 100 nm to 300 nm, a mean surface area of 240 to 250 $m^2/g$, and a type-II nitrogen adsorption-desorption BET isotherm with a H3 hysteresis loop. A method for the photocatalytic decomposition of organic pollutants using the nanoparticles is disclosed. An antibacterial composition containing the crystalline α-$Fe_2O_3$ nanoparticles is also disclosed.

8 Claims, 14 Drawing Sheets

Related U.S. Application Data continuation of application No. 16/582,693, filed on Sep. 25, 2019, now Pat. No. 11,235,983.

(51) Int. Cl.
*C30B 30/00* (2006.01)
*B82Y 30/00* (2011.01)
*B82Y 40/00* (2011.01)

(52) U.S. Cl.
CPC .......... *B82Y 40/00* (2013.01); *C01P 2002/72* (2013.01); *C01P 2002/82* (2013.01); *C01P 2004/03* (2013.01); *C01P 2004/04* (2013.01); *C01P 2004/32* (2013.01); *C01P 2004/64* (2013.01); *C01P 2006/12* (2013.01); *C01P 2006/16* (2013.01)

(56) References Cited

OTHER PUBLICATIONS

Liang, et al. ; Novel Flaxseed Gum Nanocomposites are Slow Release Iron Supplements ; Journal of Agricultural and Food Chemistry ; May 8, 2018 ; 36 Pages.

Malarkodi, et al. ; Synthesis of Fe2O3 Using Emblica officinalis Extract and its Photocatalytic Efficiency ; Material Science: An Indian Journal ; vol. 16, Issue 1 ; Feb. 28, 2018 : 10 Pages.

Alagiri, et al. ; Green synthesis of a-Fe2O3 nanoparticles for photocatalytic application ; Journal of Materials Science Materials in Electronics ; Aug. 2014 ; 7 Pages.

Gherca, et al. ; In situ surface treatment of nanocrystalline MFe2O4 (M = Co, Mg, Mn, Ni) spinel ferrites using linseed oil ; Applied Surface Science 278 ; pp. 490-498 ; Dec. 2013 ; Abstract Only ; 2 Pages.

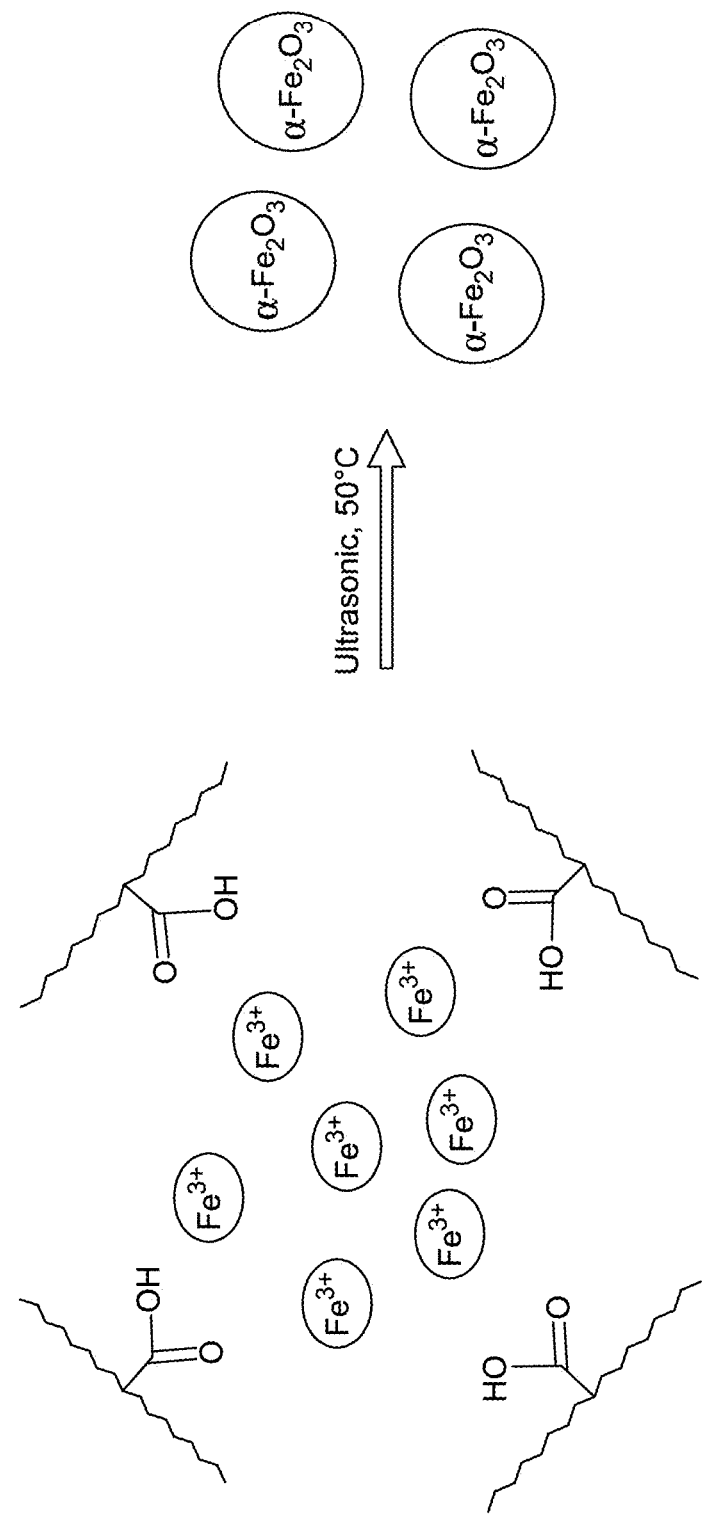

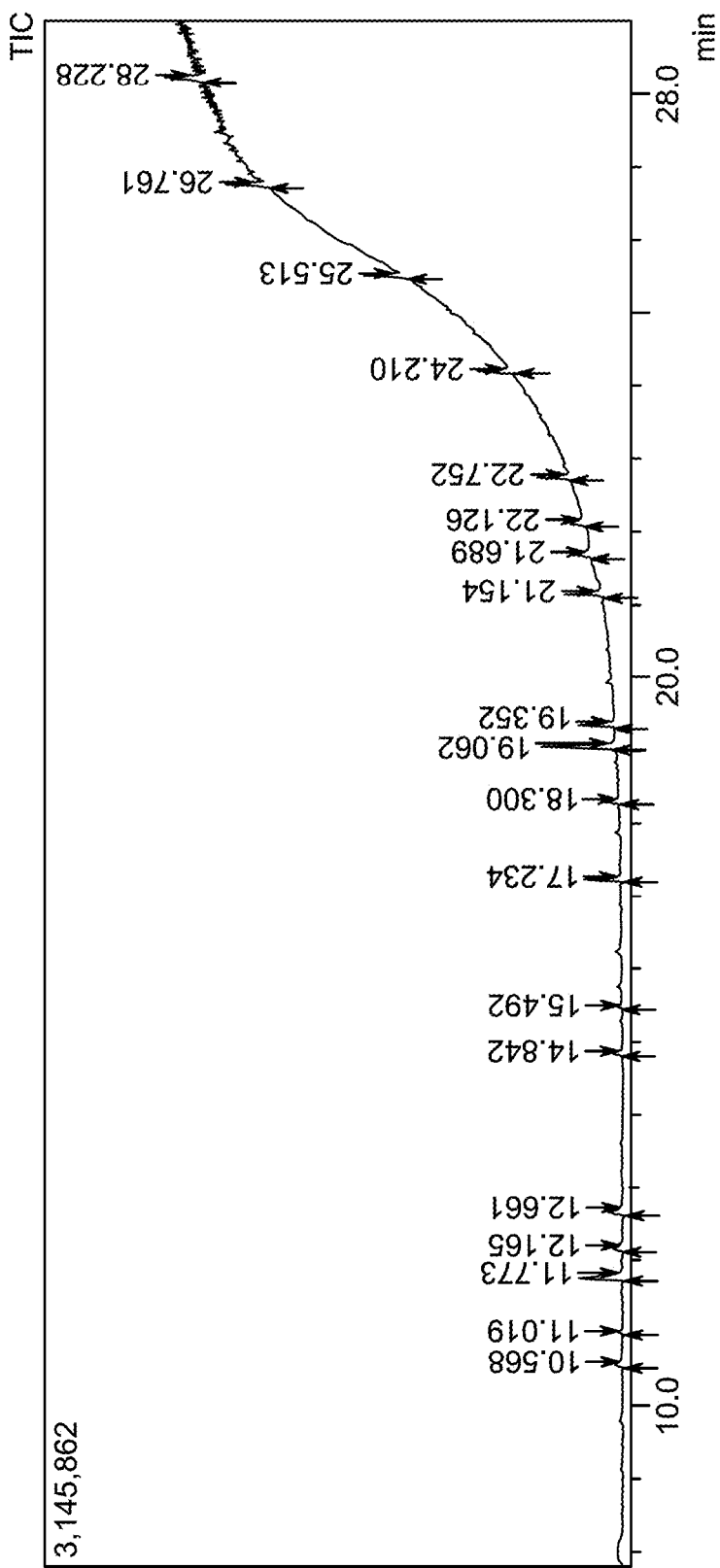

Fig. 5A.
Fig. 5B.
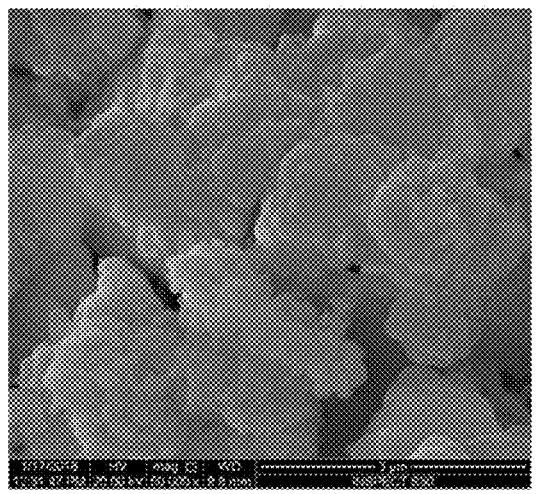
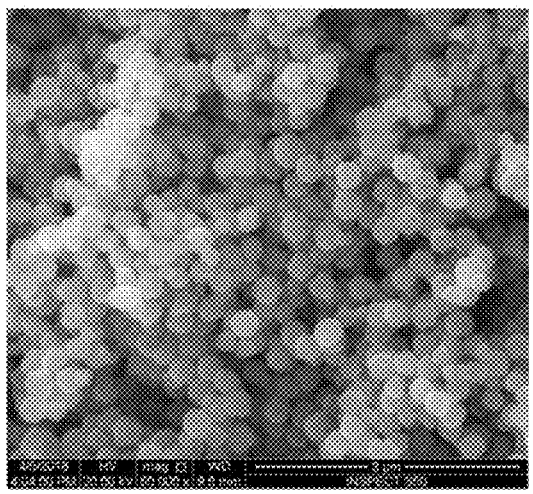
Fig. 6A.
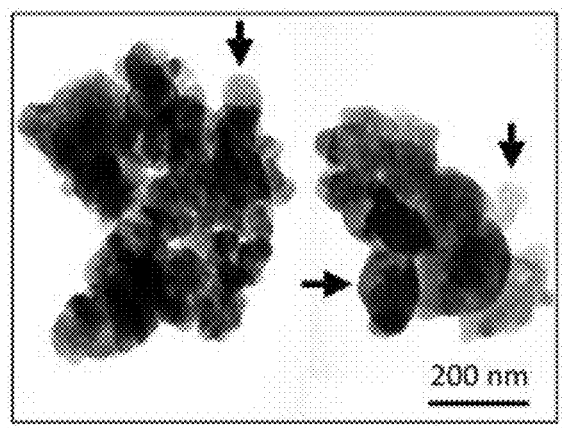
Fig. 6B.
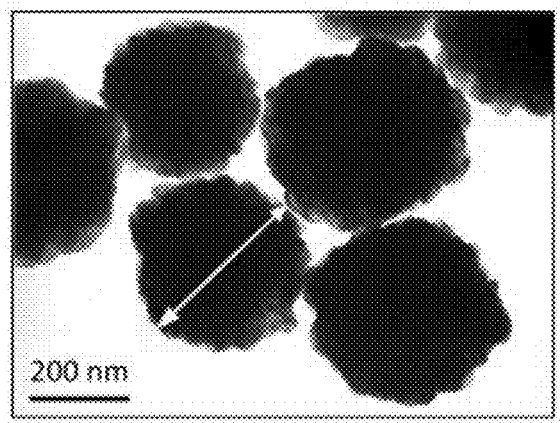

METHOD FOR TREATING POLLUTED COMPOSITION

CROSS-REFERENCE TO RELATED APPLICATIONS

The present application is a Continuation of U.S. application Ser. No. 17/543,899, now allowed, having a filing date of Dec. 7, 2021, which is a Continuation of U.S. application Ser. No. 16/582,693, now U.S. Pat. No. 11,235,983, having a filing date of Sep. 25, 2019.

BACKGROUND OF THE INVENTION

Field of the Invention

The present disclosure relates a method of preparing spherical nanoparticles of $\alpha$-$Fe_2O_3$ utilizing an extract from a seed of a plant in the family Linaceae, a method of photodegradation of organic pollutants using the nanoparticles, a photocatalyst comprising the nanoparticles, and an antibacterial composition containing the nanoparticles.

Discussion of the Background

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Recently, intensive research focus has been placed on preventing environmental degradation and promoting the optimal use of natural resources. Water remediation has become a worldwide issue, since serious health problems or death frequently result from water pollution. Several kinds of materials can cause water pollution such as herbicides, pesticides, toxic metal ions and pathogens. Several methods have been used to treat wastewater including electrochemical oxidation techniques using metal plates [Nordin, et. al., Int. J. Electrochem. Sci., 8(9), (2013), 11403-11415: Vlyssides, et. al., Waste management, 20(7), (2000), 569-574] or adsorption methods [Namasivayam, et. al., Process Saf. Environ. Prot., 85(2), (2007), 181-184].

Among various wastewater treatment methods, tremendous research efforts are being directed to photocatalytic processes using semiconductor nanomaterials such as $TiO_2$ [Mohamed, Appl. Catal. A, 541, (2017), 25-34], ZnO [Mohamed, J. Photochem. Photobiol. A, 353, (2018), 401-408], ZnS [Sharma, et. al., Solar Energy, 86, (2012), 626-633], CdO [Kumar, et. al., Mater. Lett., 151, (2015), 45-48] and $Bi_2O_3$ [Barrera-Mota, et. al., Photochem. Photobiol. Sci., 14, (2015), 1110-1119] due to their demonstrated rapid and efficient destruction of pollutants. Among semiconducting photocatalyst materials, hematite ($\alpha$-$Fe_2O_3$, bandgap~ 2.1 eV) is a promising candidate. Hematite is the most thermodynamically stable phase of iron oxide, is environmentally-friendly, has a low cost, has a high availability, and has a high resistance to corrosion [Mishram, et. al., Appl. Catal. A, 498, (2015), 126-141]. Such properties make it a promising candidate for various applications including environmental remediation and wastewater treatment. $\alpha$-$Fe_2O_3$ nanomaterials have been prepared by various chemical and physical methods including sol-gel, hydrothermal, solvothermal, sonochemical and mechanochemical synthesis [Abbas, et. al., J. Ind. Eng. Chem., 39, (2016), 112-120; Nasirian, et. al., J. Environ. Manag., 196, (2017), 487-498; and Cheng, et. al., Mater. Chem. Phys., 190, (2017), 53-61.]. These techniques have involved the use of environmentally-unfriendly chemicals, toxic organic solvents, eco-unfriendly templating agents such as pluronic123 [Sun, et. al., Adv. Mater., 17, (2005), 2993-2997] and sodium dodecyl sulfate (SDS), or energy-intensive or chemically harsh conditions. Accordingly, these methods generate hazardous by-products and involve high energy consumption. To date, little research has been done to synthesize these materials using eco-friendly/green methods and techniques.

Eco-friendly methods of synthesizing nanomaterials include using low energy techniques, such as sonication [Mohamed, J. Photochem. Photobiol. A, 353, (2018), 401-408.; and Zhang, et. al., J. Alloys Comp., 577(15), (2013), 528-532] or microwave radiation [Meng, et. al., Mater Today Chem., 1-2, (2016), 63-83] at ordinary temperature and/or using eco-friendly materials and/or precursors. The eco-friendly materials used in synthesis of nanoparticles include: whole, parts, or extracts of plants, bacteria, and/or fungi, and using water as solvent instead of organic solvents [Nabil, et. al., J Inorg Organomet Polym Mater., 28, (2018), 1552-1564; and Liu, et. al., RSC Adv., 4, (2014), 14564-14568]. Using plant extracts in nanomaterial synthesis has received more attention compared to the other eco-friendly resources, owing to its safe use, simplicity and cost effective, and therefore can be used as an economic and valuable alternative for the large-scale production of nanomaterials. Extracts from plants may act as both inducing and templating agents in nanoparticle synthesis.

The antioxidants and polyphenolic compounds in the plant/plant waste extract can act as stabilizing/templating agents and reducing agent for the synthesis of shape and size controlled nanoparticles [Alomair, et. al., Mater. Res. Express, 5, (2018), 095012].

Previously-used methods for making $\alpha$-$Fe_2O_3$ nanoparticles have either required the use of environmentally-unfriendly chemicals or techniques or have yielded products with undesirable characteristics such as low crystallinity, irregular particle shape and/or size, or low photocatalytic activity for the photodegradation of organic pollutants. Accordingly, it is one object of the invention to provide $\alpha$-$Fe_2O_3$ nanoparticles with high crystallinity and regular size and shape that show high photocatalytic activity in the photodegradation of organic pollutants as well as an environmentally-friendly method of producing the same.

SUMMARY OF THE INVENTION

The present disclosure relates to a method for producing crystalline $\alpha$-$Fe_2O_3$ nanoparticles involving ultrasonically treating a nanoparticle synthesis solution made of an iron (III)-containing precursor and a seed extract derived from a seed from a plant in the family Linaceae (Linaceae Seed Extract—LSE) at a temperature of 30 to 70° C. The method produces crystalline $\alpha$-$Fe_2O_3$ nanoparticles have a spherical shape with a diameter from 50 to 500 nm, and an average sphericity of greater than 0.94 or a cross-section or projection with an average circularity of greater than 0.94.

In some embodiments, the seed from the plant in the family Linaceae is flax seed.

In some embodiments, the LSE is produced by boiling or steeping powdered seeds from the plant in the family Linaceae in water and filtering or otherwise removing solid particles.

In some embodiments, the water used to produce the LSE has a pH of 5.5 to 8.5.

In preferred embodiments, the LSE comprises at least 4 of the following compounds: dihydroxyacetone, 2,2-oxy bisethanol, glycerin, 2-hydroxy-gamma-butyrolactone, maltol, and 3-deoxy-d-mannoic lactone and either cyclohexylmethyl hexadecyl ester or sucrose.

In preferred embodiments, the iron (III)-containing precursor is iron (III) nitrate.

In some embodiments, the nanoparticle synthesis solution is prepared by dropwise addition of the LSE to a solution of the iron (III)-containing precursor.

In preferred embodiments, the iron (III)-containing precursor is present in the solution of the iron (III)-containing precursor in an amount of 0.85 to 1.15 mol Fe(III)/L.

In some embodiments, the solution of the iron (III)-containing precursor comprises the iron (III)-containing precursor and water.

In some embodiments, the ultrasonic treatment begins before the addition of the LSE solution is complete.

In some embodiments, the nanoparticle synthesis solution is ultrasonically treated for 15 minutes to 4 hours.

In some embodiments, the nanoparticle synthesis solution is ultrasonically treated at 45 kHz and 30 to 90 W.

In some embodiments, the crystalline $\alpha$-$Fe_2O_3$ nanoparticles have a band gap of 2.10 to 2.16 eV and a surface area of 200 to 300 $m^2/g$.

In some embodiments, the crystalline $\alpha$-$Fe_2O_3$ nanoparticles have a Type II BET nitrogen adsorption-desorption curve with a H3 hysteresis loop and a mean pore size of 7.25 to 9.25 nm.

The present disclosure also relates to crystalline nanoparticles of $\alpha$-$Fe_2O_3$ having a spherical shape with a diameter from 50 to 500 nm, which have an average sphericity of greater than 0.94 or a cross-section or projection with an average circularity of greater than 0.94, a band gap of 2.10 to 2.16 eV, a surface area of 200 to 300 $m^2/g$, a Type II BET nitrogen adsorption-desorption curve with a H3 hysteresis loop, and a mean pore size of 7.25 to 9.25 nm.

In some embodiments, the nanoparticles are monodisperse, having a coefficient of variation defined as the ratio of a standard deviation of diameters to an average diameter of less than 15%.

The present disclosure also relates to a method for the photodegradation of organic pollutants involving contacting the crystalline nanoparticles of $\alpha$-$Fe_2O_3$ and an organic pollutant such as a dye, a phenol, a polycyclic aromatic hydrocarbon, an herbicide, a pesticide, or the like in a solvent to form a solution and irradiating the solution with a visible light source.

In some embodiments, the nanoparticles are present in the solution in an amount of 0.5 to 1.5 g/L.

The present disclosure also relates to a photocatalyst comprising the crystalline nanoparticles and nanoparticles of a non-iron metal oxide.

The present disclosure also relates to an antibacterial composition comprising the crystalline nanoparticles of claim 15 having a MIC value against *Staphylococcus aureus* and/or *E. Coli* of 1 to 1000 ppm.

BRIEF DESCRIPTION OF THE DRAWINGS

FIG. 2B shows the formation mechanism of $\alpha$-$Fe_2O_3$ nanospheres using LSE;

FIG. 3D shows the chromatogram of the LSE;

FIG. 5A is an SEM micrograph of the $\alpha$-$Fe_2O_3$ prepared by chemical methods in the absence of LSE;

FIG. 5B is an SEM micrograph of the eco-friendly $\alpha$-$Fe_2O_3$ prepared in the presence of LSE;

FIG. 6A is a TEM micrograph of the $\alpha$-$Fe_2O_3$ prepared by chemical methods in the absence of LSE;

FIG. 6B is a TEM micrograph of the eco-friendly $\alpha$-$Fe_2O_3$ prepared in the presence of LSE;

DETAILED DESCRIPTION OF THE INVENTION

Figure 1A:
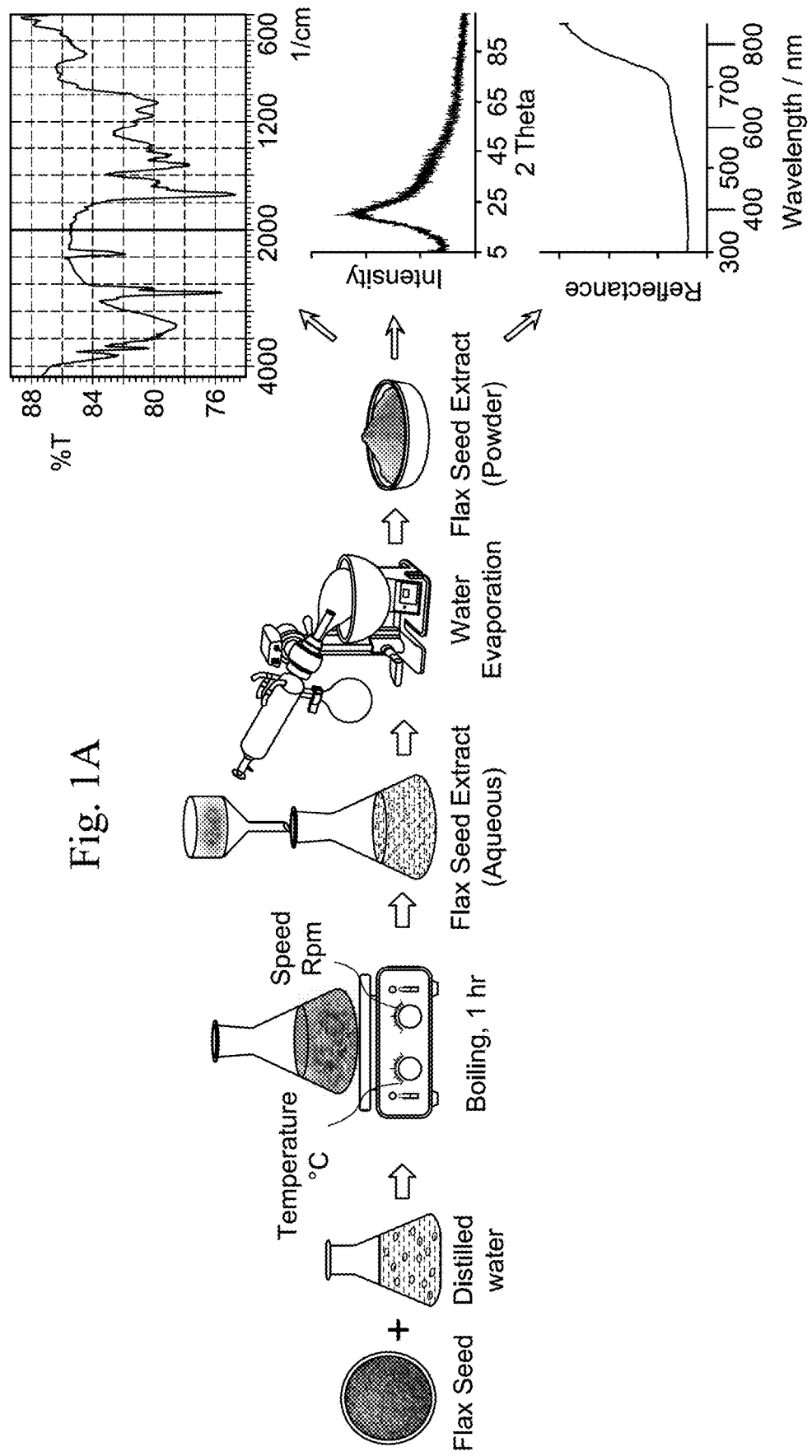
FIG. 1A shows a schematic representation of the preparation of the LSE.

In the following description, it is understood that other embodiments may be utilized and structural and operational changes may be made without departure from the scope of the present embodiments disclosed herein.

Definitions

The phrase "substantially free", unless otherwise specified, describes a particular component being present in an amount of less than about 1 wt. %, preferably less than about 0.5 wt. %, more preferably less than about 0.1 wt. %, even more preferably less than about 0.05 wt. %, yet even more preferably 0 wt. %, relative to a total weight of the composition being discussed.

As used herein, the terms "optional" or "optionally" means that the subsequently described event(s) can or cannot occur or the subsequently described component(s) may or may not be present (e.g., 0 wt. %).

As used herein, "sphericity" means a measure of how closely a shape approaches that of a mathematically perfect sphere. Sphericity may be defined as $\pi^{1/3}(6V_p)^{2/3}/A_p$, where $V_p$ is the volume of the particle and $A_p$ is the surface area of the particle.

As used herein, "circularity" means a measure of how closely a shape approaches that of a mathematically perfect circle. Circularity may be defined as $4\pi(Area)/Perimeter^2$, which may vary from 0 for a 1-dimensional object to 1 for a perfect circle.

As used herein, "inhibit" means prevent, hinder, reverse, remove, lessen, reduce an amount of, or delay the growth of.

As used herein, the term "solvothermal method" refers to a method of producing chemical compounds using a chemical reaction that takes place in a solvent other than pure water, preferably at a pressure above 1 bar and at a temperature above the boiling point of the solvent at atmospheric pressure. A solvothermal method differs from a hydrothermal method in that the latter is restricted to using only water as the solvent. Typically, if water is the only solvent used, the term hydrothermal method is preferred and solvothermal method refers solely to methods that use solvents other than or in addition to water.

As used herein, the term "surfactant" refers to a compound that lowers the surface tension (or interfacial tension) between two liquids, between a liquid and a gas, or between a liquid and a solid. The surfactant may be a nonionic surfactant, an anionic surfactant, a cationic surfactant, a viscoelastic surfactant, or a zwitterionic surfactant. The surfactant may also be a gemini surfactant of any of the types listed previously. The surfactant may serve a role as a water-wetting agent, a defoamer, a foamer, a detergent, a dispersant, or an emulsifier.

A surfactant molecule comprises one or more hydrophilic head units attached to one or more hydrophobic tails. The tail of most surfactants comprises a hydrocarbon chain, which can be branched, linear, or aromatic. Fluorosurfactants have fluorocarbon chains. Siloxane surfactants have siloxane chains. Gemini surfactant molecules comprise two or more hydrophilic heads and two or more hydrophobic tails.

Many surfactants include a polyether chain terminating in a highly polar anionic group. The polyether groups often comprise ethoxylated (polyethylene oxide-like) sequences inserted to increase the hydrophilic character of a surfactant. Alternatively, polypropylene oxides may be inserted to increase the lipophilic character of a surfactant.

Anionic surfactants contain anionic functional groups at their head, such as sulfate, sulfonate, phosphate, and carboxylate. The anionic surfactant may be an alkyl sulfate, an alkyl ether sulfate, an alkyl ester sulfonate, an alpha olefin sulfonate, a linear alkyl benzene sulfonate, a branched alkyl benzene sulfonate, a linear dodecylbenzene sulfonate, a branched dodecylbenzene sulfonate, an alkyl benzene sulfonic acid, a dodecylbenzene sulfonic acid, a sulfosuccinate, a sulfated alcohol, a ethoxylated sulfated alcohol, an alcohol sulfonate, an ethoxylated and propoxylated alcohol sulfonate, an alcohol ether sulfate, an ethoxylated alcohol ether sulfate, a propoxylated alcohol sulfonate, a sulfated nonyl phenol, an ethoxylated and propoxylated sulfated nonyl phenol, a sulfated octyl phenol, an ethoxylated and propoxylated sulfated octyl phenol, a sulfated dodecyl phenol, and an ethoxylated and propoxylated sulfated dodecyl phenol. Other anionic surfactants include ammonium lauryl sulfate, sodium lauryl sulfate (sodium dodecyl sulfate, SLS, or SDS), and related alkyl-ether sulfates sodium laureth sulfate (sodium lauryl ether sulfate or SLES), sodium myreth sulfate, docusate (dioctyl sodium sulfosuccinate), perfluorooctanesulfonate (PFOS), perfluorobutanesulfonate, alkyl-aryl ether phosphates, and alkyl ether phosphates.

Cationic surfactants have cationic functional groups at their head, such as primary and secondary amines. Cationic surfactants include octenidine dihydrochloride: cetrimonium bromide (CTAB), cetylpyridinium chloride (CPC), benzalkonium chloride (BAC), benzethonium chloride (BZT), dimethyldioctadecylammonium chloride, and dioctadecyldimethylammonium bromide (DODAB).

Zwitterionic (amphoteric) surfactants have both cationic and anionic groups attached to the same molecule. Zwitterionic surfactants include CHAPS (3-[(3-cholamidopropyl)dimethylammonio]-1-propanesulfonate), cocamidopropyl hydroxysultaine, ocamidopropyl betaine, phospholipids, and sphingomyelins.

Nonionic surfactants have a polar group that does not have a charge. These include long chain alcohols that exhibit surfactant properties, such as cetyl alcohol, stearyl alcohol, cetostearyl alcohol, oleyl alcohol, and other fatty alcohols. Other long chain alcohols with surfactant properties include polyethylene glycols of various molecular weights, polyethylene glycol alkyl ethers having the formula CH3-(CH2)10-16-(O—C2H4)1-25-OH, such as octaethylene glycol monododecyl ether and pentaethylene glycol monododecyl ether; polypropylene glycol alkyl ethers having the formula: CH3-(CH2)10-16-(O—C3H6)1-25-OH: glucoside alkyl ethers having the formula CH3-(CH2)10-16-(O-glucoside)1-3-OH, such as decyl glucoside, lauryl glucoside, octyl glucoside: polyethylene glycol octylphenyl ethers having the formula C8H17-(C6H4) (O—C2H4)1-25-OH, such as Triton X-100; polyethylene glycol alkylphenyl ethers having the formula C9H19-(C6H4)-(O—C2H4)1-25-OH, such as nonoxynol-9; glycerol alkyl esters such as glyceryl laurate: polyoxyethylene glycol sorbitan alkyl esters such as polysorbate, sorbitan alkyl esters, cocamide MEA, cocamide DEA, dodecyldimethylamine oxide, block copolymers of polyethylene glycol and polypropylene glycol, such as poloxamers, and polyethoxylated tallow amine (POEA).

A dendritic surfactant molecule may include at least two lipophilic chains that have been joined at a hydrophilic center and have a branch-like appearance. In each dendritic surfactant, there may be from about 2 lipophilic moieties independently to about 4 lipophilic moieties attached to each hydrophilic group, or up to about 8 lipophilic moieties attached to the hydrophilic group for example. "Independently" as used herein with respect to ranges means that any lower threshold may be combined with any upper threshold. The dendritic surfactant may have better repulsion effect as a stabilizer at an interface and/or better interaction with a polar oil, as compared with other surfactants. Dendritic surfactant molecules are sometimes called "hyperbranched" molecules.

A dendritic extended surfactant is a dendritic surfactant having a non-ionic spacer arm between the hydrophilic group and a lipophilic tail. For example, the non-ionic spacer-arm extension may be the result of polypropoxylation, polyethoxylation, or a combination of the two with the polypropylene oxide next to the tail and polyethylene oxide next to the head. The spacer arm of a dendritic extended surfactant may contain from about 1 independently to about 20 propoxy moieties and/or from about 0 independently to about 20 ethoxy moieties. Alternatively, the spacer arm may contain from about 2 independently up to about 16 propoxy moieties and/or from about 2 independently up to about 8 ethoxy moieties. "Independently" as used herein with respect to ranges means that any lower threshold may be combined with any upper threshold. The spacer arm extensions may also be formed from other moieties including, but not necessarily limited to, glyceryl, butoxy, glucoside, isosorbide, xylitols, and the like. For example, the spacer arm of a dendritic extended surfactant may contain both propoxy and ethoxy moieties. The polypropoxy portion of the spacer arm may be considered lipophilic: however, the spacer arm may also contain a hydrophilic portion to attach the hydrophilic group. The hydrophilic group may generally be a polyethoxy portion having about two or more ethoxy groups. These portions are generally in blocks, rather than being randomly mixed. Further, the spacer arm extension may be a poly-propylene oxide chain.

Another type of surfactant is a viscoelastic surfactant (VES). Conventional surfactant molecules are characterized by having one long hydrocarbon chain per surfactant headgroup. In a viscoelastic gelled state these molecules aggregate into worm-like micelles. A viscoelastic gel is a gel that has elastic properties, meaning that the gel at least partially returns to its original form when an applied stress is removed. Typical viscoelastic surfactants include N-erucyl-N,N-bis(2-hydroxyethyl)-N-methyl ammonium chloride and potassium oleate, solutions of which form gels when mixed with inorganic salts such as potassium chloride and/or with organic salts such as sodium salicylate. Previously described surfactants may also be considered viscoelastic surfactants.

Method for Preparing Crystalline $\alpha$-$Fe_2O_3$ Nanoparticles

According to a first aspect, the present disclosure relates to methods of making crystalline $\alpha$-$Fe_2O_3$ nanoparticles. Generally, the method involves ultrasonication techniques whereby a solution of an iron (III)-containing precursor and a seed extract derived from a seed from a plant in the family Linaceae (Linaceae Seed Extract—LSE) are treated ultrasonically at a temperature below the normal boiling point of water (100° C.). One advantage of the disclosed methods is that the $\alpha$-$Fe_2O_3$ nanoparticles can be formed with regular size and morphology without the need for temperatures above 100° C. in contrast to hydrothermal or solvothermal methods, caustic or toxic chemicals such as concentrated strong bases (e.g. NaOH, KOH, or $NH_4OH$), nor does the presently disclosed method require an additional high temperature (e.g. 700° C.) calcination step [Lassoued, et. al., Results in Physics, 7, (2017), 3007-3015; and Nasirian, et. al., J. Environ. Manag., 196, (2017), 487-498].

A nanoparticle synthesis solution comprising an iron (III)-containing precursor and a seed extract derived from a seed from a plant in the family Linaceae (LSE) is treated ultrasonically at a temperature of 30 to 70° C., preferably 35 to 65° C., preferably 40 to 60° C., preferably 45 to 55° C., preferably 50° C. for a time of 15 minutes to 4 hours, preferably 30 minutes to 3.5 hours, preferably 45 minutes to 3 hours, preferably 1 hour to 2.5 hours, preferably 1.5 hours to 2.25 hours, preferably 2 hours to form a suspension. In preferred embodiments, the ultrasonic treatment is performed at 30 to 60 kHz, preferably 35 to 55 kHz, preferably 40 to 50 KHz, preferably 45 kHz and 30 to 90 W, preferably 45 to 75 W, preferably 60 W. Following the ultrasonication treatment step, the nanoparticles may be collected by any solid-liquid separation technique known to those of ordinary skill in the art, for example, filtration, decantation, centrifugation, or the like, but excluding techniques such as evaporation. In preferred embodiments, the nanoparticles are collected by centrifugation at 500 to 5000 rpm, preferably 750 to 4500 rpm, preferably 1000 to 4000 rpm to form a pellet. In some embodiments, this pellet may be washed with a wash solvent to remove any impurities from the crystalline $\alpha$-$Fe_2O_3$ nanoparticles. In preferred embodiments the wash solvent is one in which $\alpha$-$Fe_2O_3$ has a solubility below 0.1 g per 100 mL, preferably below 0.05 g per 100 mL, preferably below 0.01 g per 100 mL, preferably below 0.005 g per 100 mL, preferably below 0.001 g per 100 mL, preferably below 0.00064 g per 100 mL of solvent at 25° C. Examples of such wash solvents include but are not limited to distilled water, methanol, ethanol, and acetone. In some embodiments, the pellet is washed more than one time. In preferred embodiments, the pellet is washed with no more than one wash solvent. In some embodiments, the pellet may be washed with additional wash solvents, but preferably they are not. In preferred embodiments, the wash solvent is distilled water and the pellet is washed with distilled water two times. In some embodiments, the pellet may be redispersed in the wash solvent using a technique known to those of ordinary skill in the art, for example, stirring, vortex mixing, shaking, or ultrasonication. Following such a redispersal, the nanoparticles may be collected by centrifugation as described above. Such a cycle of pelleting, redispersing in a wash solvent, and centrifugation constitutes one washing. Following the washings, the pellet may be dried, for example, by allowing the pellet to dry in ambient atmosphere, an inert atmosphere, or by subjecting the pellet tor vacuum. In some embodiments, the pellet is dried at room temperature. In preferred embodiments, the pellet is dried at 30 to 100° C., preferably 40 to 90° C., preferably 60 to 80° C., preferably at 70° C. In some embodiments, the pellet may be dried for 1 minute to 24 hours, preferably 5 minutes to 18 hours, preferably 15 minutes to 12 hours, preferably 30 minutes to 6 hours, preferably 45 minutes to 3 hours, preferably 1 hour.

In some embodiments, the LSE is produced by boiling or steeping powdered seeds from the plant in the family Linaceae in water to produce a seed extract suspension, then filtering or using another method known to those of ordinary skill in the art to remove solid particles from the seed extract suspension to produce the LSE. In preferred embodiments, the LSE is produced by boiling in water. In preferred embodiments, water is the only solvent present in the production of the LSE. While other solvents, such as methanol, ethanol, acetone, or similar organic solvents may be used, preferably they are not. While other solvents may be added to the water to form a mixture of water and another solvent, preferably they are not. In preferred embodiments, the water used to produce the LSE has a pH of 5.5 to 8.5, preferably 6 to 8, preferably 6.5 to 7.5, preferably 7. In preferred embodiments, the water used in the extraction is substantially free of a surfactant. In preferred embodiments, the LSE is an aqueous extract. An aqueous extract is an extract produced with water with a neutral pH of 6.75 to 7.25 and that is substantially free of other components. An aqueous extract is distinct from an alcoholic extract such as a methanolic extract or an ethanolic extract by using only water as the extraction solvent, not pure or aqueous solutions of alcohols. An aqueous extract is distinct from an acidic extract in that the water used in an aqueous extract has a neutral pH, not an acidic pH. An aqueous extract is distinct from a basic extract in that the water used in an aqueous extract has a neutral pH, not a basic pH. An aqueous extract is distinct from a surfactant-assisted extract in that the water used in an aqueous extract does not contain a surfactant at the time of the contact between the water and the material to be extracted. The use of acids, bases, organic solvents, or surfactants may change the composition of the LSE and may be disadvantageous to the use in the method described herein.

In some embodiments, the powdered seeds are boiled for 1 minute to 6 hours, preferably 5 minutes to 5 hours, preferably 15 minutes to 4 hours, preferably 30 minutes to 3 hours, preferably 45 minutes to 2 hours, preferably 1 hour.

Plants in the family Linaceae include, but are not limited to plants in the genus: *Anisadenia* such as *A. khasyana*, *A. pubescens*, and *A. saxatillis*: *Hesperolinon* (also known as dwarf-flax or western flax) such as *H. adenophyllum* (glandular western flax), *H. bicarpellatum* (bicarpellate western flax), *H. breweri* (brewer's western flax), *H. californium* (California western flax), *H. clevelandii* (Allen Springs dwarf flax), *H. congestum* (Marin western flax), *H. didymocarpum* (Lake County western flax), *H. disjunctum* (Coast Range western flax), *H. drymarioides* (drymary western flax), *H. micranthum* (smallflower western flax), *H. sharsmithiae* (Sharsmith's western flax), *H. spergulinum* (slender western flax), and *H. tehamense* (Tehama western flax); *Cliococca* such as *C. selaginoides*; *Linum* (also known as flax) such as *L. alatum* (winged flax), *L. album*, *L. alpinum*, *L arenicola* (sand flax), *L. aristatum* (bristle flax), *L. australe* (southern flax), *L. austriacum* (Asian flax), *L. berlandieri* (Berlandier's yellow flax), *L. bienne* (pale flax), *L. campanulatum*, *L. carteri* (Carter's flax), *L. catharticum* (fairy flax), *L. compactum* (Wyoming flax), *L. cratericola* (Galapagos Islands flax), *L. dolomiticum*, *L. elongatum* (Laredo flax), *L. flavum* (golden flax), *L. floridanum* (Florida yellow flax), *L. grandiflorum* (scarlet or flowering flax), *L. hirsutum* (downy flax), *L. hudsonioides* (Texas flax), *L. imbricatum* (tufted flax), *L. intercursum* (sandplain flax), *L. kingii* (King's flax), *L. leoni*, *L. lewisii* (Lewi's flax or Lewis's blue flax), *L. lundellii* (Sullivan City flax), *L. macrocarpum* (Spring Hill flax), *L. marginale* (Australian native flax), *L. medium* (stiff yellow flax), *L. monogynum* (New Zealand linen flax), *L. narbonense* (blue flax), *L. neomexicanum* (New Mexico yellow flax), *L. perenne* (perennial blue flax), *L. pratense* (meadow flax), *L. puberulum* (plains flax), *L. pubescens*, *L. rigidum* (stiffstem flax), *L. rupestre* (rock flax), *L. schiedeanum* (Schiede's flax), *L. strictum* (ridged yellow flax), *L. subteres* (Sprucemont flax or slenderfoot flax), *L. suffruticosum*, *L. sulcatum* (grooved flax), *L. tenuifolium*, *L. trigynum* (French flax), *L. usitatissimum* (common cultivated flax), *L. vernal* (Chihuahuan flax), *L. virginianum* (woodland flax), and *L. westii* (West's flax); *Reinwardita* such as *R. indicta* (yellow flax); *Sclerolinon* such as *S. digynum* (northwestern yellowflax); *Tirpitzia* such as *T. ovoidea* and *T. sinensis*; *Durandea* such as *D. angustifolia*, *D. deplanchei*, *D. jenkinsii*, *D. latifolia*, *D. oreogena*, *D. racemose*, *D. viscosa*, and *D. vitiensis*: *Hebepetalum* such as *H. humiriifolia*, *H. neblinae*, and *H. roraimense*; *Hugonia* such as *H. afzelii*, *H. batesii*, *H. breweriodes*, *H. castanea*, *H. coursiana*, *H. gabunensis*, *H. gilletii*, *H. gossweileri*, *H. johannensis*, *H. longipes*, *H. macrocarpa*, *H. macrophylla*, *H. mayumbensis*, *H. micans*, *H. mystax* (climbing flax), *H. obtusifolia*, *H. orientalis*, *H. planchonii*, *H. platysepala*, *H. rufopilis*, *H. sapinii*, *H. sphaerocarpa*, *H. spicata*, *H. talbotii*, and *H. villosa*; *Indorouchera* such as *I. griffithiana*: *Philbornea* such as *P. magnifolia*: and *Roucheria* such as *R. calophylla*, *R. columbiana*, *R. laxiflora*, *R. schomburgkii*, and *R. sipapoensis*. In preferred embodiments, the plant in the family Linaceae is a flax. A flax is a member of the genus *Linum* (also known as flaxes) or a plant in the family Linaceae with a common name which includes flax, examples of which are provided above.

In preferred embodiments, the LSE comprises at least 4 of the following components, preferably at least 5 of the following components, preferably all 6 of the following components: dihydroxyacetone, 2,2-oxy bisethanol, glycerin, 2-hydroxy-gamma-butyrolactone, maltol, and 3-deoxy-d-manoic lactone. In preferred embodiments, the LSE additionally comprises either, preferably both, cyclohexylmethyl hexadecyl ester, and/or sucrose. These components may be advantageous for use in the method by providing an OH source and/or templating agent for $\alpha$-$Fe_2O_3$ nanoparticle formation.

In preferred embodiments, the solution of the iron(III)-containing precursor comprises the iron (III)-containing precursor and a precursor solution solvent. In preferred embodiments, the precursor solution solvent is water. While other solvents may be used, preferably they are not. In preferred embodiments, the iron (III)-containing precursor is an iron (III)-containing compound that has a solubility in water of greater than 28 g/100 mL, preferably greater than 98 g/100 mL, preferably greater than 110 g/100 mL, preferably greater than 125 g/100 mL, preferably greater than 137 g/100 ml of water at 20° C. In preferred embodiments, the iron (III)-containing precursor is iron (III) nitrate. In preferred embodiments, the iron (III)-containing precursor is present in the solution of the iron (III)-containing precursor in an amount of 0.85 to 1.15 mol Fe(III)/L, preferably 0.90 to 1.10 mol Fe(III)/L, preferably 0.95 to 1.05 mol Fe(III)/L, preferably 1.00 mol Fe(III)/L. In preferred embodiments, the solution of the iron (III)-containing precursor consists essentially of or consists of water and the iron (III)-containing precursor. In preferred embodiments, the solution of the iron (III)-containing precursor is substantially free of other components.

In some embodiments, the nanoparticle synthesis solution is prepared by mixing one of the constituent solutions with the other (i.e. mixing the LSE into the solution of the iron (III)-containing precursor or the solution of the iron (III)-containing precursor into the LSE). In some embodiments, the nanoparticle synthesis solution is prepared by dropwise addition of one of the constituents to the other (i.e. the LSE to the solution of the iron (III)-containing precursor or the solution of the iron (III)-containing precursor to the LSE). In preferred embodiments, the dropwise addition is of the LSE to the solution of the iron (III)-containing precursor. In some embodiments, the ultrasonication treatment begins before the addition of the LSE to the solution of the iron (III)-containing precursor is complete. In preferred embodiments, the ultrasonication begins after the first drop of the LSE is added to the solution of the iron (III)-containing precursor. In preferred embodiments, the dropwise addition occurs over a period of 15 minutes to 5 hours, preferably 30 minutes to 4 hours, preferably one hour to 3 hours, preferably 2 hours.

In preferred embodiments, the method produces crystalline $\alpha$-$Fe_2O_3$ nanoparticles that have a spherical shape, having a diameter of 50 to 500 nm, preferably 75 to 400 nm, preferably 100 to 300 nm. In preferred embodiments, the crystalline $\alpha$-$Fe_2O_3$ nanoparticles have an average sphericity of greater than 0.94, preferably greater than 0.95, preferably greater than 0.96, preferably greater than 0.97, preferably greater than 0.975, preferably greater than 0.98, preferably greater than 0.99. Because the sphericity calculation involves characteristics that may be difficult or impractical to measure for nanoparticles in certain embodiments, the corresponding 2D equivalent, circularity, may be used to characterize the shape of the crystalline $\alpha$-$Fe_2O_3$ nanoparticles. In such cases, the crystalline $\alpha$-$Fe_2O_3$ nanoparticles preferably have a cross section or projection with an average circularity of greater than 0.94, preferably greater than 0.95, preferably greater than 0.96, preferably greater than 0.97, preferably greater than 0.975, preferably greater than 0.98, preferably greater than 0.99. Such a cross section or projection may be obtained from electron microscopy data. In preferred embodiments, the crystalline α-$Fe_2O_3$ nanoparticles are monodisperse with a coefficient of variation, defined as the ratio of the standard deviation to the mean diameter, of less than 15%, preferably less than 10%, preferably less than 9%, preferably less than 8%, preferably less than 7%, preferably less than 6%, preferably less than 5%, preferably less than 4%, preferably less than 3%, preferably less than 2%. In preferred embodiments, the crystalline α-$Fe_2O_3$ nanoparticles have a uniform shape with a sphericity coefficient of variation, defined as the ratio of the standard deviation to the mean sphericity, of less than 15%, preferably less than 10%, preferably less than 9%, preferably less than 8%, preferably less than 7%, preferably less than 6%, preferably less than 5%, preferably less than 4%, preferably less than 3%, preferably less than 2%. In preferred embodiments, the crystalline α-$Fe_2O_3$ nanoparticles have a uniform shape with a cross section or projection that has a circularity coefficient of variation, defined as the ratio of the standard deviation to the mean circularity, of less than 15%, preferably less than 10%, preferably less than 9%, preferably less than 8%, preferably less than 7%, preferably less than 6%, preferably less than 5%, preferably less than 4%, preferably less than 3%, preferably less than 2%.

In some embodiments, the crystalline α-$Fe_2O_3$ nanoparticles show a spherical morphology that has small bumps, protrusions, lobes, or globular shapes on the surface of the nanoparticle. In some embodiments, these bumps, protrusions, lobes, or globular shapes form an ordered or irregular arrangement on the surface of the nanoparticle. In some embodiments, these bumps, protrusions, lobes, or globular shapes have a maximum height measured tangentially from the surface of the sphere of 10%, preferably 7.5%, preferably 5%, preferably 2.5% of the overall diameter of the nanoparticle. In some embodiments, an individual particle has a number of bumps, protrusions, lobes, or globular shapes from 10 to 120, preferably 12 to 92, preferably 24 to 62, preferably 32 to 60.

In preferred embodiments, the crystalline α-$Fe_2O_3$ nanoparticles are mesoporous as determined by $N_2$ adsorption-desorption measurements or equivalent methods known to those of ordinary skill in the art. In preferred embodiments, the crystalline α-$Fe_2O_3$ nanoparticles have a Type II BET nitrogen adsorption-desorption curve with an $H3$ hysteresis loop. In preferred embodiments, the crystalline α-$Fe_2O_3$ nanoparticles have a mean pore diameter of 7.25 to 9.25 nm, preferably 7.5 to 9 nm, preferably 7.75 to 8.75 nm, preferably 8 to 8.5 nm. In preferred embodiments, the pores have a total pore volume of $1\times10^{-2}$ to $50\times10^{-2}$ cc/g, preferably $2\times10^{-2}$ to $25\times10^{-2}$ cc/g, preferably $5\times10^{-2}$ to $15\times10^{-2}$ cc/g, preferably $7.5\times10^{-2}$ to $12.5\times10^{-2}$ cc/g. In preferred embodiments, the crystalline α-$Fe_2O_3$ nanoparticles have a surface area of 100 to 400 $m^2/g$, preferably 200 to 300 $m^2/g$, preferably 210 to 290 $m^2/g$, preferably 220 to 280 $m^2/g$, preferably 230 to 270 $m^2/g$, preferably 240 to 260 $m^2/g$.

In preferred embodiments, the crystalline α-$Fe_2O_3$ nanoparticles have a band gap of 2.10 to 2.16 eV, preferably 2.11 to 2.15 eV, preferably 2.12 to 2.14 eV, preferably 2.13 eV. This band gap may be determined by a method known to those of ordinary skill in the art. One such method is to use diffuse reflectance spectroscopy to determine the reflectance of a solid sample. This reflectance may be related to the absorbance by the Kubelka-Munk relation to produce a Kubelka-Munk function. A plot of this Kubelka-Munk function vs photon energy allows for a tangent to be drawn at the absorption edge to calculate the value of the onset of absorption, which gives the value of the band gap.

Method for Photodegradation of Organic Pollutants

The crystalline α-$Fe_2O_3$ nanoparticles produced by the method above may find use in a method for photodegrading organic pollutants. Such a method involves mixing together the crystalline α-$Fe_2O_3$ nanoparticles and an organic pollutant in a solvent to form a solution, followed by irradiation of that solution with a visible light source. The crystalline nature, mesoporous nature, high surface area, band gap value, or chemical composition of the nanoparticles produced by the above method may be advantageous in accelerating the rate of or creating conditions or species that cause the photodegradation of organic pollutants. In preferred embodiments, this mixing step takes place in a solvent which can dissolve the organic pollutant. In preferred embodiments, the nanoparticles are present in an amount of 500 to 1500 ppm, preferably 600 to 1400 ppm, preferably 700 to 1300 ppm, preferably 800 to 1200 ppm, preferably 900 to 1100 ppm, preferably 1000 ppm based on the total amount of the reaction mixture.

In some embodiments, crystalline α-$Fe_2O_3$ nanoparticles are mixed in a solvent. Solvents that may be used include an aprotic organic solvent, a protic organic solvent, or preferably, water. Examples of aprotic organic solvents include but are not limited to diethyl ether, tetrahydrofuran, acetonitrile, acetone, N,N-dimethylformamide, dimethylsulfoxide, pentane, hexanes, cyclohexane, benzene, toluene, chloroform, dichloromethane, and ethyl acetate. Examples of protic organic solvents include but are not limited to ammonia, t-butanol, n-butanol, n-propanol, 2-propanol, ethanol, and methanol. In some embodiments, the aprotic organic solvent or protic organic solvent is substantially free of water, oxygen, or both. In preferred embodiments, the solvent is water. In some embodiments, the water is substantially free of dissolved salts or other electrolytes. In some embodiments, the water is taken directly from an environmental source such as an ocean, sea, bay, river, stream, lake, pond, or the like. In some embodiments, the water is salt water (also known as seawater) as found in an ocean, sea, bay, or other source. In some embodiments, the water is freshwater (also known as fresh water) as found in a naturally occurring source such as ice sheet, ice cap, glacier, bog, pond, lake, river, stream, underground reservoir, or the like. In some embodiments, the water is brackish water. In preferred embodiments, the water has not been deoxygenated by a method intended to remove dissolved oxygen gas from the water. In preferred embodiments, the water has oxygen gas dissolved at a concentration of 0.1 to 50 ppm, preferably 0.5 to 30 ppm, preferably 1 to 20 ppm, preferably 2 to 16 ppm.

In some embodiments the visible light source is the sun. In some embodiments, the visible light source is an artificial light source. Examples of artificial light sources include, but are not limited to an incandescent lamp, an argon flash lamp, a carbide lamp, gas lighting, a kerosene lamp, an oil lamp, an arc lamp, a flashtube, a gas discharge lamp, an electrodeless lamp, an excimer lamp, a fluorescent lamp, a carbon arc lamp, a ceramic discharge metal-halide lamp, a mercury-vapor lamp, a sodium-vapor lamp, a xenon arc lamp, a neon lamp, a plasma lamp, an LED, a light-emitting electrochemical cell, an electroluminescent material, a laser including, but not limited to chemical, dye, free-electron, gas, ion, diode, metal-vapor, quantum well, ruby, and solid-state type lasers, and a deuterium arc lamp. In some embodiments, the artificial light source is a sunlight simulating light source. In preferred embodiments, the light source has a spectral power distribution with a normalized power at 570 to 590 nm, calculated by taking the power at a given wavelength divided by the power at a reference wavelength (typically a wavelength of 555 to 560 nm), of greater than 0.2, preferably greater than 0.3, preferably greater than 0.4, preferably greater than 0.5.

In some embodiments, the organic pollutants may be a dye, a phenol, a polycyclic aromatic hydrocarbon, an herbicide, a pesticide, a persistent organic pollutant, or the like.

In some embodiments, the organic pollutant is a dye. A dye is a colored substance that chemically binds to a material it may be intended to color. Generally, a dye is applied in solution, typically aqueous solution. Examples of dyes include, but are not limited to: acridine dyes, which are acridine and its derivatives such as acridine orange, acridine yellow, acriflavine, and gelgreen: anthraquinone dyes, which are anthroaquinone and its derivatives such as acid blue 25, alizarin, anthrapurpurin, carminic acid, 1,4-diamno-2,3-dihydroanthraquinone, 7,14-dibenzypyrenequinone, dibromoanthrone, 1,3-dihydroxyanthraquinone, 1,4-dihydroxyanthraquinone, disperse red 9, disperse red 11, indanthrone blue, morindone, oil blue 35, parietin, quinizarine green SS, remazol brilliant blue R, solvent violet 13, 1,2,4-trihydroxyanthraquinone, vat orange 1, and vat yellow 1; diaryl methane dyes such as auramine O, triarylmethane dyes such as acid fuchsin, aluminon, aniline blue WS, aurin, aurintricarboxylic acid, brilliant blue FCF, brilliant green, bromocresol green, bromocresol purple, bromocresol blue, bromophenol blue, bromopyrogallol red, chlorophenol red, coomassie brilliant blue, cresol red, O-cresolphthalein, crystal violet, dichlorofluorescein, ethyl green, fast green FCT, FlAsH-EDT2, fluoran, fuchsine, green S, light green SF, malachite green, merbromin, metacresol purple, methyl blue, methyl violet, naphtholphthalein, new fuchsine, pararosaniline, patent blue V, phenol red, phenolphthalein, phthalein dye, pittacal, spirit blue, thymol blue, thymolphthalein, Victoria blue BO, Victoria blue R, water blue, xylene cyanol, and xylenol orange: azo dyes such as acid orange 5, acid red 13, alican yellow, alizarine yellow R, allura red AC, amaranth, amido black 10B, aniline yellow, arylide yellow, azo violet, azorubine, basic red 18, biebrich scarlet, Bismarck brown Y, black 7984, brilliant black BN, brown FK, chrysoine resorcinol, citrus red 2, congo red, D&C red 33, direct blue 1, disperse orange 1, eriochrome black T, evans blue, fast yellow AB, orange 1, hydroxynaphthol blue, janus green B, lithol rubine BK, metanil yellow, methyl orange, methyl red, methyl yellow, mordant brown 33, mordant red 19, naphthol AS, oil red O, oil yellow DE, orange B, orange G, orange GGN, para red, pigment yellow 10, ponceau 2R, prontosil, red 2G, scarlet GN, Sirius red, solvent red 26, solvent yellow 124, sudan black B, sudan I, sudan red 7B, sudan stain, tartrazine, tropaeolin, trypan blue, and yellow 2G: phthalocyanine dyes such as phthalocyanine blue BN, phthalocyanine Green G, Alcian blue, and naphthalocyanine, azin dyes such as basic black 2, mauveine, neutral red, Perkin's mauve, phenazine, and safranin; indophenol dyes such as indophenol and dichlorophenolindophenol: oxazin dyes: oxazone dyes: thiazine dyes such as azure A, methylene blue, methylene green, new methylene blue, and toluidine blue: thiazole dyes such as primuline, stains-all, and thioflavin; xanthene dyes such as 6-carboxyfluorescein, eosin B, eosin Y, erythosine, fluorescein, rhodamine B, rose bengal, and Texas red; fluorone dyes such as calcein, carboxyfluorescein diacetate succinimidyl ester, fluo-3, fluo-4, indian yellow, merbromin, pacific blue, phloxine, and seminaphtharhodafluor; or rhodamine dyes such as rhodamine, rhodamine 6G, rhodamine 123, rhodamine B, sulforhodamine 101, and sulforhodamine B.

A phenol is an organic compound consisting of a hydroxyl group (—OH) bonded directly to an aromatic hydrocarbon group. Examples of phenols include, but are not limited to, phenol (the namesake of the group of compounds), bisphenols (including bisphenol A), butylated hydroxytoluene (BHT), 4-nonylphenol, orthophenyl phenol, picric acid, phenolphthalein and its derivatives mentioned above, xylenol, diethylstilbestrol, L-DOPA, propofol, butylated hydroxyanisole, 4-tert-butylcatechol, tert-butylhydroquinone, carvacrol, chloroxyleol, cresol (including M-, O-, and P-cresol), 2,6-di-tert-butylphenol, 2,4-dimethyl-6-tert-butylphenol, 2-ethyl-4,5-dimethylphenol, 4-ethylguaiacol, 3-ethylphenol, 4-ethylphenol, flexirubin, mesitol, 1-nonyl-4-phenol, thymol, 2,4,6-tri-tert-butylphenol, chlorophenol (including 2-, 3-, and 4-chlorophenol), dichlorophenol (including 2,4- and 2,6-dichlorophenol), bromophenol, dibromophenol (including 2,4-dibromophenol), nitrophenol, norstictic acid, oxybenzone, and paracetamol (also known as acetoaminophen).

A polycyclic aromatic hydrocarbon (PAH) is an aromatic hydrocarbon composed of multiple aromatic rings. Examples of polycyclic aromatic hydrocarbons include naphthalene, anthracene, phenanthrene, phenalene, tetracene, chrysene, triphenylene, pyrene, pentacene, benzo[a]pyrene, corannulene, benzo[g,h,i]perylene, coronene, ovalene, benzo[c]fluorine, acenaphthene, acenaphthylene, benz[a]anthracene, benzo[b]fluoranthene, benzo[j]fluoranthene, benzo[k]fluoranthene, benzo[e]pyrene, cyclopenta[c,d]pyrene, dibenz[a,h]anthracene, dibenzo[a,e]pyrene, dibenzo[a,h]pyrene, dibenzo[a,i]pyrene, dibenzo[a,l]pyrene, fluoranthene, fluorine, indeno[1,2,3-c,d]pyrene, 5-methylchrysene, naphthacene, pentaphene, picene, and biphenylene.

An herbicide (also known as "weedkiller") is a substance that is toxic to plants and may kill, inhibit the growth of, or prevent the germination of plants. Herbicides are typically used to control the growth of or remove unwanted plants from an area of land, particularly in an agricultural context. Examples of herbicides include, but are not limited to, 2,4-D, aminopyralid, chlorsulfuron, clopyralid, dicamba, diuron, glyphosate, hexazinone, imazapic, imazapyr, methsulfuron methyl, picloram, sulfometuron methyl, triclopyr, fenoxaprop, fluazifop, quizalofop, clethodim, sethoxydim, chlorimuron, foramsulfuron, halosulfuron, nicosulfuron, primisulfuron, prosulfuron, rimsulfuron, thofensulfuron, tribenuron, imazamox, imazaquin, flumetsulam, cloransulam, thiencarbazone, fluoxpyr, diflufenzopyr, atrazine, simazine, metribuzin, bromoxynil, bentazon, linuron, glufosinate, clomazone, isoxaflutole, topramezone, mesotrione, tembotrione, acifluorfen, formesafen, lactofen, flumiclorac, flumioxazin, fulfentrazone, carfentrazone, fluthiacet-ethyl, falufenacil, paraquat, ethalfluralin, pendimethalin, trifluralin, butylate, EPTC, ecetochlor, alachlor, metolachlor, dimethenamid, flufenacet, and pyroxasulfone.

A pesticide is a substance meant to prevent, destroy, or control pests including, but not limited to algae, bacteria, fungi, plants, insects, mites, snails, rodents, and viruses.

A pesticide intended for use against algae is known as an algaecide. Examples of algaecides include benzalkonium chloride, bethoxazin, cybutryne, dichlone, dichlorophen, diuron, endothal, fentin, isoproturon, methabenthiazuron, nabam, oxyfluorfen, pentachlorophenyl laurate, quinoclamine, quinonamid, simazine, terbutryn, and tiodonium.

A pesticide intended for use against bacteria is known as a bactericide. Examples of bactericides include antibiotics such as: aminoglycosides such as amikacin, gentamicin, kanamycin, neomycin, netilmicin, tobramycin, paromomycin, streptomycin, and spectinomycin: ansamycins such as geldanamycin, herbimycin, and rifaximin: carbacephems such as loracarbef; carbapenems such as ertapenem, doripenem, imipenem, and meropenem; cephalosporins such as cefadroxil, cefazolin, cephradine, cephapirin, cephalothin, cephalexin, cefaclor, cefoxitin, cefotetan, cefamandole, cefmetazole, cefonicid, cefprozil, cefuroxime, cefixime, cefdinir, cefditoren, cefoperazone, cefotaxime, cefpodoxime, cefazidime, ceftibuten, ceftizoxime, moxalactam, ceftriaxone, cefepime, cefaroline fosamil, and ceftobiprole: glycopeptides such as teicoplanin, vancomycin, telavancin, dalbavancin, and oritavancin: lincosamides such as clindamycin and lincomycin: lipopeptides such as daptomycin: macrolides such as azithromycin, clarithromycin, erythromycin, roxithromycin, telithromycin, spiramycin, and fidoxamicin; monobactams such as aztreonam; nitrofurans such as furazolidone and nitrofurantoin; oxazolidinones such as linezolid, posizolid, radezolid, and torezolid: penicillins such as amoxicillin, ampicillin, azlocillin, dicloxacillin, flucloxacillin, mezlocillin, methicillin, nafcillin, oxacillin, penicillins (including penicillin G and V), piperacillin, temocillin, and ticarcillin: polypeptides such as bacitracin, colistin, and polymyxin B: quinolones such as ciproflaxacin, enoxacin, gatifloxacin, gemifloxacin, levofloxacin, lomefloxacin, moxifloxacin, nadifloxacin, nalidixic acid, norfloxacin, ofloxacin, trovafloxacin, gepafloxacin, sparfloxacin, and temafloxacin; sulfonamides such as mafenide, sulfacetamide, sulfadiazine, sulfadithoxine, sulfamethizole, sulfamethoxazole, sulfanilamide, sulfasalazine, sulfisoxazole, and sulfonamidochrysoidine; tetracyclines such as demeclocycline, doxycycline, metacycline, minocycline, oxytetracycline, and tetracycline.

A pesticide intended for use against fungi is known as a fungicide. Examples of fungicides include acibenzolar, acypetacs, aldimorph, anilazine, aureofungin, azaconazole, azithiram, azoxystrobin, benalaxyl, benodanil, benomyl, benquinox, benthiavalicarb, binapacryl, biphenyl, bitertanol, bixafen, blasticidin-S, boscalid, bromuconazole, captafol, captan, carbendazim, carboxin, carpropamid, chloroneb, chlorothalonil, chlozolinate, cyazofamid, cymoxanil, cyprodinil, dichlofluanid, diclocymet, dicloran, diethofencarb, difenoconazole, diflumetorim, dimethachlone, dimethomorph, diniconazole, dinocap, dodemorph, edifenphos, enoxastrobin, epoxiconazole, etaconazole, ethaboxam, ethirimol, etridiazole, famoxadone, fenamidone, fenarimol, fenbuconazole, fenfuram, fenhexamid, fenoxanil, fenpropidin, fenpropimorph, ferbam, fluazinam, fludioxonil, flumorph, fluopicolide, fluopyram, fluoroimide, fluoxastrobin, flusilazole, flutianil, flutolain, flopet, fthalide, furalaxyl, guazatine, hexaconazole, hymexazole, imazalil, imibenconazole, iminoctadine, iodocarb, ipconazole, iprobenfos, iprodione, iprovalicarb, siofetamid, isoprothiolane, isotianil, kasugamycin, laminarin, mancozeb, mandestrobin, mandipropamid, maneb, mepanypyrim, mepronil, meptyldinocap, mealaxyl, metominostrobin, metconazole, methafulfocarb, metiram, metrafenone, myclobutanil, naftifine, nuarimol, octhilinone, ofurace, orysastrobin, oxadixyl, oxathiapiprolin, oxolinic acid, oxpoconazole, oxycarboxin, oxytetracycline, pefurazate, penconazole, pencycuron, penflufen, penthiopyrad, phenamacril, picarbutrazox, picoxystrobin, piperalin, polyoxin, probenzole, prochloraz, procymidone, propamocarb, propiconazole, propineb, proquinazid, prothiocarb, prothioconazole, pydiflumetofen, pyraclostrobin, pyrametostrobin, pyraoxystrobin, pyrazophos, pyribencarb, pyributicarb, pyrifenox, pyrimethanil, pyrimorph, pyriofenone, pyroquilon, quinoxyfen, quintozene, sedaxane, silthiofam, simeconazole, spiroxamine, streptomycin, tebuconazole, tebufloquin, teclofthalam, tecnazene, terbinafine, tetraconazole, thiabendazole, thifluzamide, thiphanate, thiram, tiadinil, tolclosfos-methyl, folfenpyrid, tolprocarb, tolylfluanid, triadimefon, triadimenol, triazoxide, triclopyricarb, tricyclazole, tridemorph, trifloxystrobin, triflumizole, triforine, validamycin, and vinclozolin.

A pesticide intended for use against plants is known as an herbicide as described above.

A pesticide intended for use against insects is known as an insecticide. Examples of insecticides are: organochlorides such as Aldrin, chlordane, chlordecone, DDT, dieldrin, endofulfan, endrin, heptachlor, hexachlorobenzene, lindane, methoxychlor, mirex, pentachlorophenol, and TDE; organophosphates such as acephate, azinphos-methyl, bensulide, chlorethoxyfos, chlorpyrifos, diazinon, chlorvos, dicrotophos, dimethoate, disulfoton, ethoprop, fenamiphos, fenitrothion, fenthion, malathion, methamdophos, methidathion, mevinphos, monocrotophos, naled, omethoate, oxydemeton-methyl, parathion, phorate, phosalone, phosmet, phostebupirim, phoxim, pirimiphos-methyl, profenofos, terbufos, and trichlorfon; carbamates such as aldicarb, bendiocarb, carbofuran, carbaryl, dioxacarb, fenobucarb, fenoxycarb, isoprocarb, methomyl: pyrethroids such as allethrin, bifenthrin, cyhalothrin, cypermethrin, cyfluthrin, deltamethrin, etofenprox, fenvalerate, permethrin, phenothrin, prallethrin, resmethrin, tetramethrin, tralomethrin, and transfluthrin; neonicotinoids such as acetamiprid, clothiandin, imidacloprid, nithiazine, thiacloprid, and thiamethoxam: ryanoids such as chlorantraniliprole, cyanthaniliprole, and flubendiamide.

A pesticide intended for use against mites is known as a miticide. Examples of miticides are permethrin, ivermectin, carbamate insecticides as described above, organophosphate insecticides as described above, dicofol, abamectin, chlorfenapyr, cypermethrin, etoxazole, hexythiazox, imidacloprid, propargite, and spirotetramat.

A pesticide intended for use against snails and other mollusks is known as a molluscicide. Examples of molluscicides are metaldehyde and methiocarb.

A pesticide intended for use against rodents is known as a rodenticide. Examples of rodenticides are warfarin, coumatetralyl, difenacoum, brodifacoum, flocoumafen, bromadiolone, diphacinone, chlorophacinone, pindone, difethialone, cholecalciferol, ergocalciferol, ANTU, chloralose, crimidine, 1,3-difluoro-2-propanol, endrin, fluroacetamide, phosacetim, pyrinuron, scilliroside, strychnine, tetramethylenedisulfotetramine, bromethalin, 2,4-dinitrophenol, and uragan D2.

A pesticide intended for use against viruses is known as a virucide. Examples of virucides are cyanovirin-N, griffithsin, interferon, NVC-422, scytovirin, urumin, virkon, zonroz, and V-bind viricie.

A persistent organic pollutant is a toxic organic chemical that adversely affects human and environmental health, can be transported by wind and water, and can persist for years, decades, or centuries owing to resistance to environmental degradation by natural chemical, biological, or photolytic processes. Persistent organic pollutants are regulated by the United Nations Environment Programme 2001 Stockholm Convention on Persistent Organic Pollutants. Examples of persistent organic pollutants are Aldrin, chlordane, dieldrin, endrin, heptachlor, hexachlorobenzene, mirex, toxaphene, polychlorinated biphenyl (PCBs), dichlorodiphenyltrichloroethane (DDT), dioxins, polychlorinated dibenzofurans, chlordecone, hexachlorocyclohexane (α- and β-), hexabromodiphenyl ether, lindane, pentachlorobenzene, tetrabromodiphenyl ether, perfluorooctanesulfonic acid, endosulfans, and hexabromocyclododecane.

Antibacterial Composition

In preferred embodiments, the crystalline $\alpha\text{-Fe}_2\text{O}_3$ nanoparticles show antibacterial activity against both gram-positive and gram-negative bacteria. The mesoporous nature, high surface area, and/or photocatalytic activity of the nanoparticles produced by the method may be advantageous for antibacterial effects. In preferred embodiments, the crystalline $\alpha\text{-Fe}_2\text{O}_3$ nanoparticles have a minimum inhibitory concentration, defined as the lowest concentration that will inhibit visible growth of a microorganism after overnight incubation, of 1 to 1000 ppm, preferably 2 to 750 ppm, preferably 3 to 500 ppm, preferably 4 to 300 ppm, preferably 5 to 250, preferably 7.5 to 200, preferably 10 to 150 ppm. In preferred embodiments, the crystalline $\alpha\text{-Fe}_2\text{O}_3$ nanoparticles have a minimum bactericidal concentration, defined as the lowest concentration that will prevent the growth of an organism after subculture on to antibiotic-free media, of 1 to 1000 ppm, preferably 2 to 750 ppm, preferably 3 to 500 ppm, preferably 4 to 250 ppm, preferably 5 to 100 ppm.

The crystalline $\alpha\text{-Fe}_2\text{O}_3$ nanoparticles produced by the method described above may find use in an antibacterial composition. These nanoparticles may be used as a component in an antibacterial composition that takes the form of a solid, liquid, gel, foam, dispersion, colloid, or other type of mixture. In some embodiments, the nanoparticles are homogenously distributed throughout the volume of the mixture. In some embodiments, the nanoparticles are non-homogenously distributed throughout the volume of the mixture. In some embodiments, the nanoparticles may separate from other components of the mixture and require mixing or redispersion before use.

In some embodiments, the antibacterial composition is intended for use in in conjunction with exposure to visible wavelengths of light. In some embodiments, the antibacterial composition has a mode of action that results from the photocatalytic properties of the nanoparticles. In some embodiments, the antibacterial composition is dissolvable or dispersible in water and may form a component of a water purification composition. When used as a component of such a water purification composition, the nanoparticles may be removed from the water or left in the water. In such an application, the nanoparticles may, in addition to acting in the antibacterial composition, also act in another composition such as one that removes other substances from water that may be undesirable.

Iron oxides (red, yellow, and black) are currently approved as "exempt from certification" as direct food additives and are "Generally Recognized as Safe" as indirect food additives by the US FDA and are approved for use as a food additive in the European Union (E172). The antibacterial composition comprising the nanoparticles may find use as a food additive. In some embodiments, the nanoparticles may be added directly to a foodstuff to form an antibacterial composition that comprises the nanoparticles and the components of the foodstuff. In some embodiments, the antibacterial composition is pre-formed from other components before being added to the foodstuff.

Iron oxide is currently a common component in many cosmetics and bath products. The antibacterial composition may also find use in such products. In some embodiments, the antibacterial composition comprising the nanoparticles is such a cosmetic or bath product. In some embodiments, the antibacterial composition is a component of a cosmetic or bath product that shows antibacterial activity. Examples of such cosmetics or bath products include but are not limited to soaps, facial soaps, facial washes, body washes, shampoos, conditioners, deodorants, antiperspirants, combination deodorants/antiperspirants, fragrances, foot powders, hair dyes or colors, makeup, nail products, personal cleanliness products, shaving products, depilatories, skincare products, tanning products, body or face creams, moisturizers, and anti-acne products.

In some embodiments, the antibacterial composition is not intended for bodily contact or ingestion. In some embodiments, the antibacterial composition is intended to be used in a container, pipe, reservoir, or other such vessel intended to store or transport material, or on a surface. In some embodiments the antibacterial composition is designed to be transiently contacted with the vessel or surface and then removed. In some embodiments, the antibacterial composition is designed to be in contact with the vessel or surface for an extended period of time including the lifetime of either the antibacterial composition or the vessel or surface. In some embodiments, the vessel or surface may allow the nanoparticles to be illuminated by visible wavelengths of light.

In some embodiments, the antibacterial composition further comprises a surfactant. A surfactant may be present at a weight percentage in a range of 0.02-10 wt %, preferably 0.1-5 wt %, more preferably 0.5-2 wt %. Examples of surfactants and surfactants types that may be included in the antibacterial composition may be those surfactants/surfactant types described previously.

In one embodiment, the antibacterial composition may further comprise a mutual solvent. A mutual solvent may be present at a weight percentage of 1-20 wt %, preferably 3-15 wt %, more preferably 4-12 wt %. As defined herein, a "mutual solvent" is a liquid that is substantially soluble in both aqueous and oleaginous fluids, and may also be soluble in other well treatment fluids. As defined here, "substantially soluble" means soluble by more than 10 grams mutual solvent per liter fluid, preferably more than 100 grams per liter. Mutual solvents are routinely used in a range of applications, controlling the wettability of contact surfaces before and preventing or stabilizing emulsions.

Examples of the mutual solvent include propylene glycol, ethylene glycol, diethylene glycol, glycerol, and 2-butoxyethanol. In a preferred embodiment, the mutual solvent is 2-butoxyethanol, which is also known as ethylene glycol butyl ether (EGBE) or ethylene glycol monobutyl ether (EGMBE). In alternative embodiments, the mutual solvent may be one of lower alcohols such as methanol, ethanol, 1-propanol, 2-propanol, n-butanol, n-hexanol, 2-ethylhexanol, and the like, other glycols such as dipropylene glycol, polyethylene glycol, polypropylene glycol, polyethylene glycol-polyethylene glycol block copolymers, and the like, and glycol ethers such as 2-methoxyethanol, diethylene glycol monomethyl ether, and the like, substantially water/oil-soluble esters, such as one or more C2-esters through C10-esters, and substantially water/oil-soluble ketones, such as one or more C2-C10 ketones.

In some embodiments, the antibacterial composition may further comprise a buffer. As used herein, a buffer (more precisely, pH buffer or hydrogen ion buffer) refers to a mixture of a weak acid and its conjugate base, or vice versa. Its pH changes very little when a small or moderate amount of strong acid or base is added to it and thus it is used to prevent changes in the pH of a solution. Buffer solutions are used as a means of keeping pH at a nearly constant value in a wide variety of chemical applications. Examples of buffers include, but are not limited to, HEPES buffer, TAPS, Bicine, Glycylglycine, Tris, HEPPSO, EPPS, HEPPS, POPSO, N-ethylmorpholine, TEA (Triethanolamine), Tricine, TAPSO, DIPSO, TES, BES, phosphoric acid, MOPS, imidazole PIPES and the like.

In one embodiment, the antibacterial composition may further comprise other components, such as alcohols, glycols, organic solvents, fragrances, dyes, dispersants, non-buffer pH control additives, acids or bases, water softeners, bleaching agents, foaming agents, antifoaming agents, catalysts, corrosion inhibitors, corrosion inhibitor intensifiers, viscosifiers, diverting agents, oxygen scavengers, carrier fluids, fluid loss control additives, friction reducers, stabilizers, rheology modifiers, gelling agents, scale inhibitors, breakers, salts, crosslinkers, salt substitutes, relative permeability modifiers, sulfide scavengers, fibers, microparticles, bridging agents, shale stabilizing agents (such as ammonium chloride, tetramethyl ammonium chloride, or cationic polymers), clay treating additives, polyelectrolytes, non-emulsifiers, freezing point depressants, iron-reducing agents, other biocides/bactericides and the like, provided that they do not interfere with the antibacterial activity of the nanoparticles as described herein.

The examples below are intended to further illustrate protocols for preparing and characterizing the nanoparticles, preparing and characterizing the LSE, performing the photodegradation, and preparing and characterizing the antibacterial composition, and are not intended to limit the scope of the claims.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

Examples

Experimental
Preparation of Flax Seed Extract (FSE)

Figure 1B:
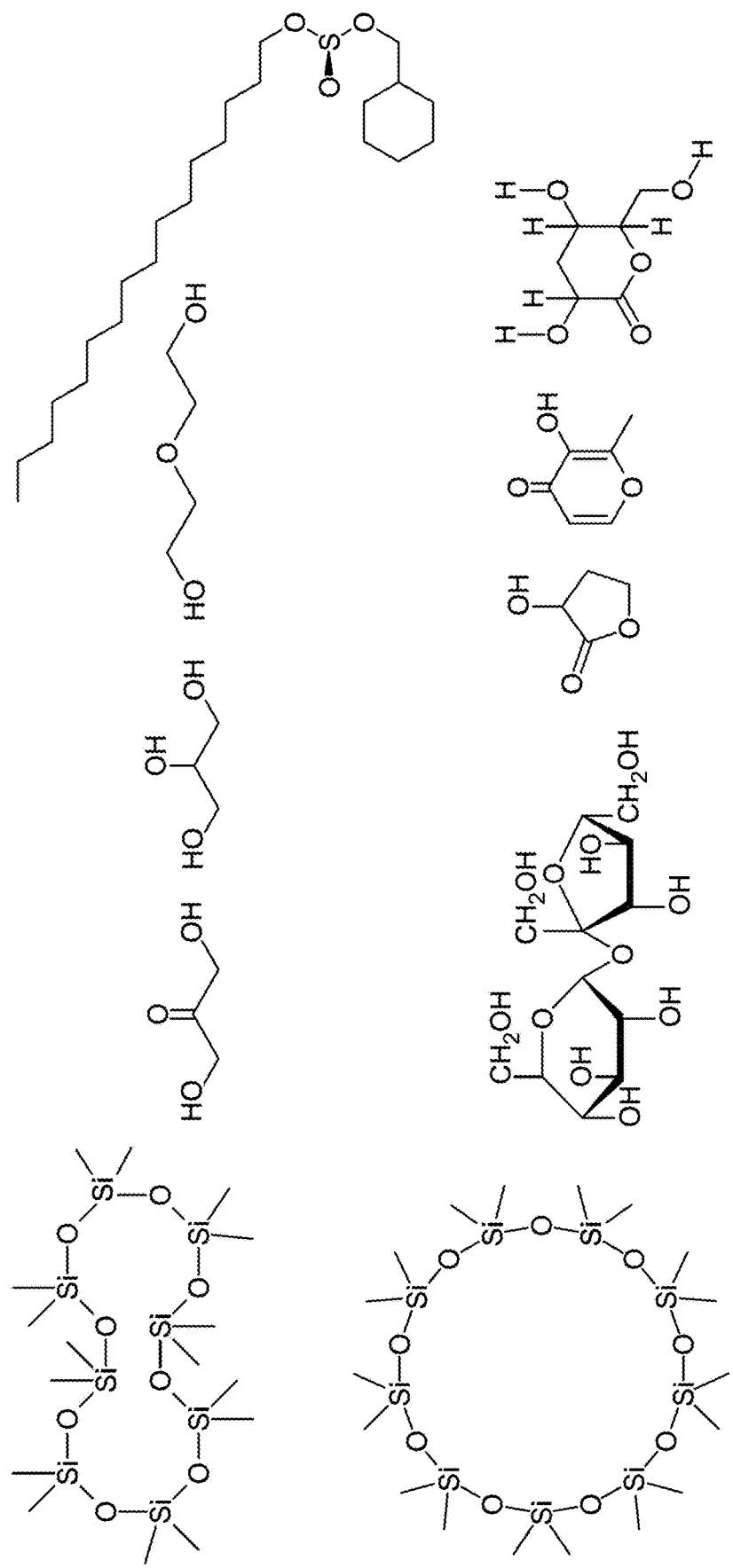
FIG. 1B shows chemical compounds present in the LSE.

The Flax Seeds (FS) was provided from local paddy mill in western region, Egypt. It was washed with distilled water, and then dried in the air. The dried seed was then ground to a fine powder. 50 g of the fine FS powder was suspended in 750 ml distilled water and the resulted FS suspension was boiled for 1 hour under reflux condition. The resulted gelatinous Flax Seed Extract (FSE—also referred to herein as Linaceae Seed Extract LSE) suspension was then filtered to remove the solid particles and then stored in the fridge. To obtain the powder of FSE, the FSE suspension was evaporated using rotary evaporator at 25° C. and 20 mbar, resulted in shiny, yellowish crystals which were then characterized using FTIR, XRD and UV-Vis diffuse Reflectance. Additionally, the solid extract was dissolved in methanol, and the GC-MS measurement was performed. The schematic representation of FSE preparation is depicted in FIG. 1.

Eco-Friendly Synthesis of $Fe_2O_3$ Nanospheres

Pure $Fe_2O_3$ nanoparticles were synthesized via sonochemical method using Iron III Nitrate ($Fe(NO_3)_3 \cdot 9H_2O$, 99.99%) as $\alpha$-$Fe_2O_3$ precursor and FSE as OH source as well as templating agent. In a typical synthesis, 5.0 g Iron Nitrate was dissolved in 20 ml distilled water and the resulted solution was transferred to the ultrasonic bath (USC200T, VWR International: 45 kHz, 60 W). 20 mL of FSE suspension was drop-wise added to the Fe III solution under ultrasonic vibration at 50° C. for 2 hours. After ultrasonic treatment, the solid products were separated from the formed suspension by centrifugation, washed two times by distilled water using centrifugation and then dried at 70°C for 1 hour (see FIG. 2). For comparison $\alpha$-$Fe_2O_3$ was prepared by chemical method using 2 M $NH_4OH$ and hydrothermal treatment.

Figure 2A:
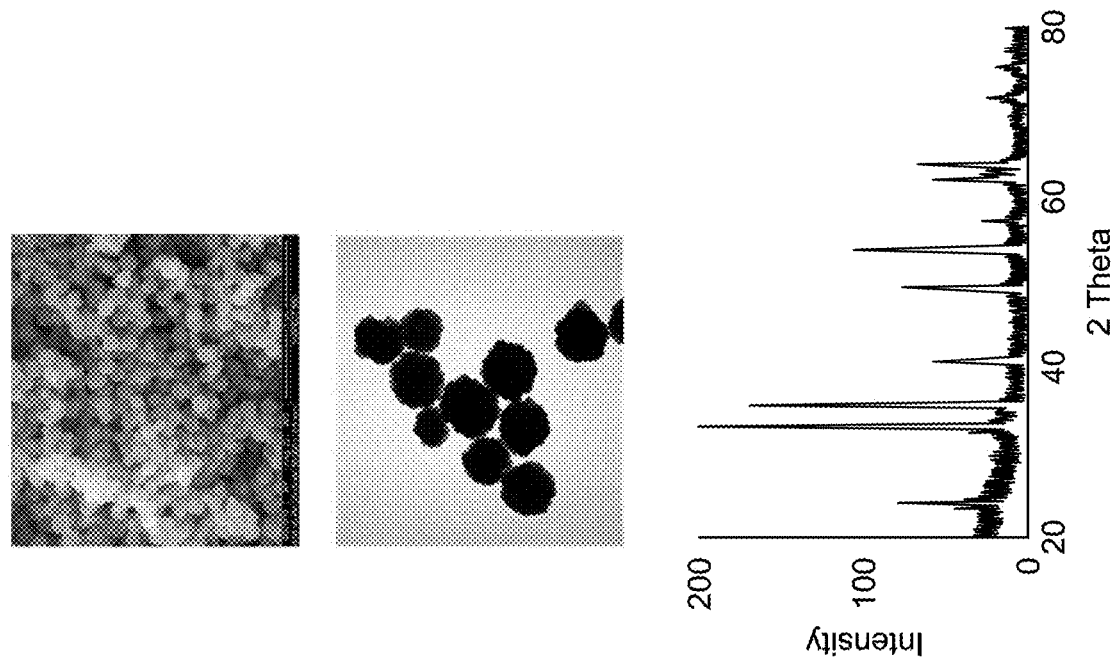
FIG. 2A shows a schematic representation of the preparation of $\alpha$-$Fe_2O_3$ nanospheres.
Figure 2A:
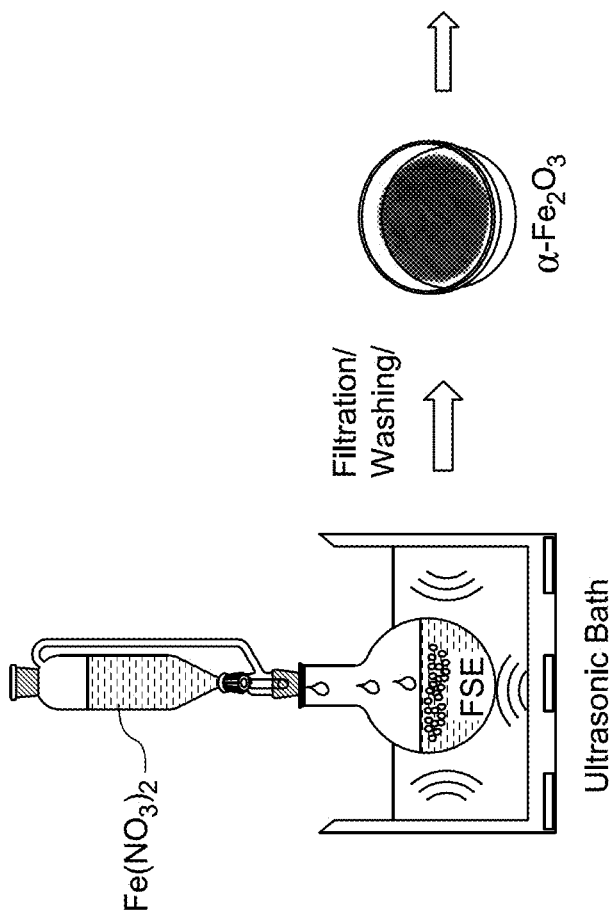

The schematic presentation of preparation of $\alpha$-$Fe_2O_3$ Nano spheres using FSE is depicted in FIG. 2A and the mechanism of preparation of $\alpha$-$Fe_2O_3$ Nano spheres using FSE is depicted in FIG. 2B and can be described by the following equation:

$$Fe^{3+} + OH - [FES] \rightarrow 2Fe(OH)_3 \xrightarrow{Ultrasonic,\ 50°C.} \alpha - Fe_2O_3 + 3H_2O \quad \text{(Eq. 1)}$$

Photocatalytic Activity

The photocatalytic performance of the green $\alpha$-$Fe_2O_3$ nanospheres has been evaluated for the degradation of the organic dye Methylene Blue (MB) as a model water pollutant. The photocatalytic experiments were carried out using sunlight simulating lamp (PT2192, 125 W). 1 g/l of the photocatalyst was dispersed in 100 mL followed by dissolving 20 ppm of MB dye. The resulting suspension was kept in the dark for 30 min under stirring to achieve equilibrium. After that, the suspension was irradiated and liquid samples were taken before and during the irradiation then centrifuged to separate the solid catalyst. The concentration of MB was determined by the UV-Vis absorption measurement.

Results and Discussion

Characterization of Flax Seed Extract (FSE)

Figure 3A:
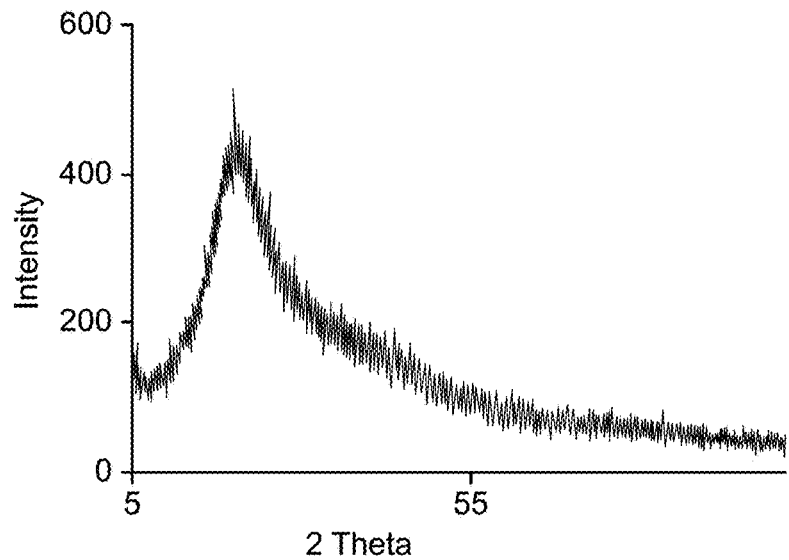
FIG. 3A shows the XRD pattern of the LSE.
Figure 3B:
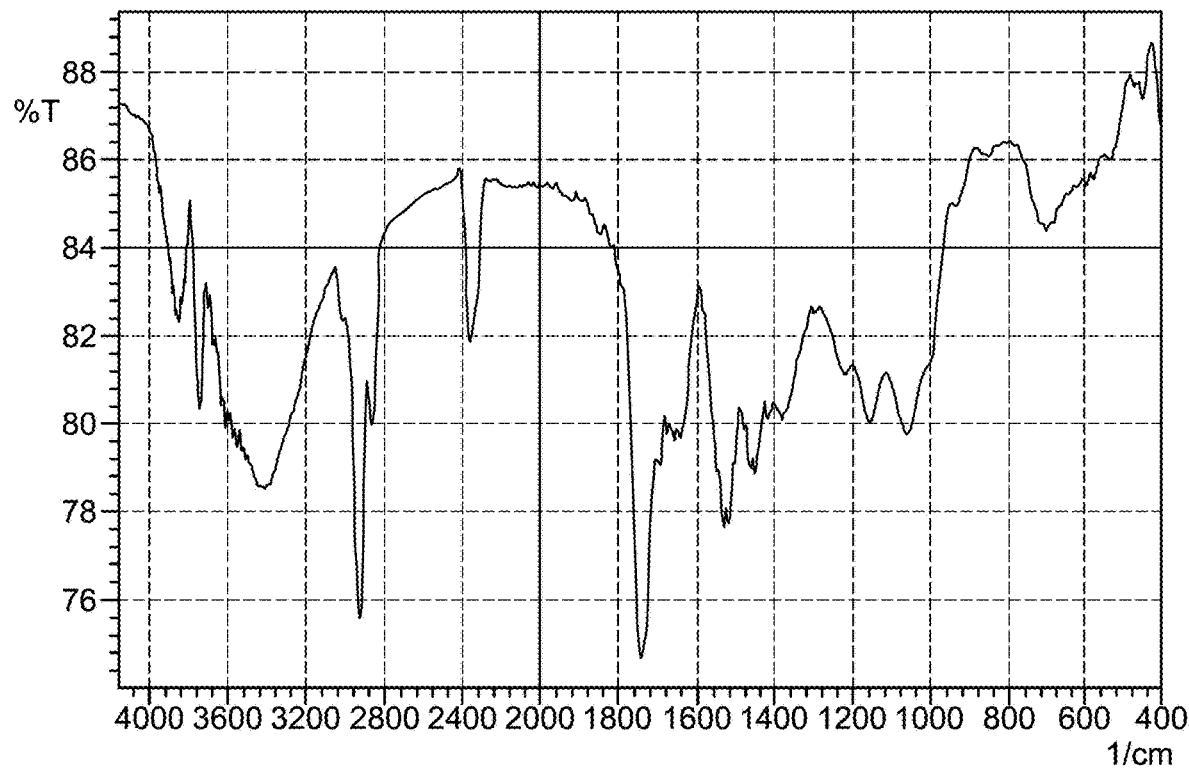
FIG. 3B shows the FTIR spectrum of the LSE.
Figure 3C:
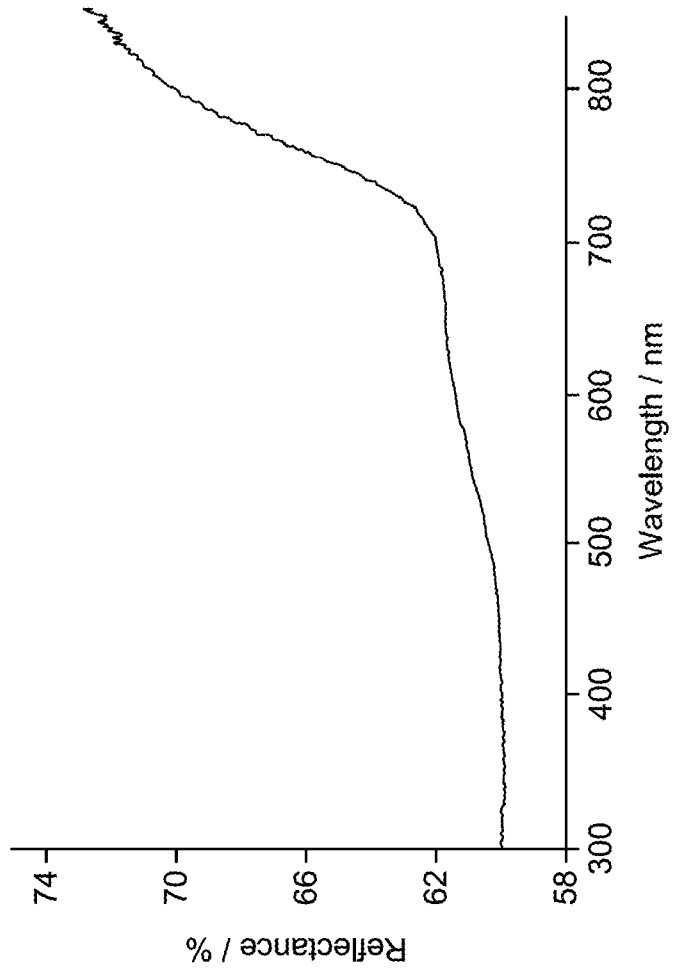
FIG. 3C shows the diffuse reflectance spectrum of the LSE.

The XRD, FTIR and UV-vis Diffuse Reflectance of the as-obtained FSE solid powder were measured. FIG. 3A shows the XRD pattern of the as obtained FSE crystals. Sharp band at 20.8° is observed which might be resulted from some bioorganic compounds present in the FSE. FIG. 3B shows the FTIR spectrum of the as obtained FSE. The strong peaks at 1504 cm-1 and at 1721 cm-1 might be assigned to ester O—$CH_3$ stretching vibration and ester carbonyl C=O stretching vibration respectively. The peak at 1148 $cm^{-1}$ represents the coupled C—C and C—O vibrations, indicated the presence of carbohydrate. The broad absorption peaks from 3600 to 3200 $cm^{-1}$ are assigned to —OH group and the peak at 2900 $cm^{-1}$ assigned to C—H stretching vibration [Elzey, et. al., Food Control, 68, (2016), 303-309—incorporated here by reference]. The presence of —OH group could corroborate the presence of polyphenolic and phenolic glycosides which act as inducing and templating agents for the synthesis of the nanomaterials [Butsat, et. al., Food Chem., 119, (2010), 606-613; and Goufo, et. al., Food Sci. Nutr., 2(2), (2014), 75-104—incorporated here by reference]. The optical properties of FSE were obtained from UV-vis Diffuse Reflectance measurement (FIG. 3C), showing broad absorption in the visible region which may be due to the antioxidants in the FSE.

The GC-MS measurements of Flax Seed Extract confirm that, it mainly contains polyphenolic compounds, esters, carbohydrate, and cyclononasiloxane compounds (FIG. 3D). Owing to these compounds, the water soluble extract of Flax Seed exhibits strong antioxidant activity. These antioxidants are responsible for the formation and stabilization of the nanomaterials. According to the GC-MS measurements the main compounds in FSE are summarized in Table 1.

TABLE 1

Chemical compounds in the FSE as obtained from GC-MS measurements.

| Compound Name/Retention Time (min) | Detailed Information | Function |
|---|---|---|
| Dihydroxyacetone/10.563 | 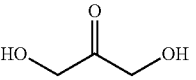 | |
| Ethanol, 2,2'-oxybis/11.015 | 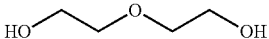 | |
| Glycerin/11.771 | 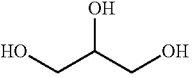 | |
| 2-Hydroxy-gamma-butyrolactone/12.167 | 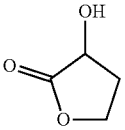 | OH source for $Fe_2O_3$ formation and Templating Agent |
| Maltol/12.665 | 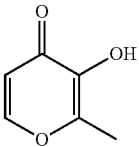 | |
| 3-Deoxy-d-mannoic lactone/21.16, 21.68 | 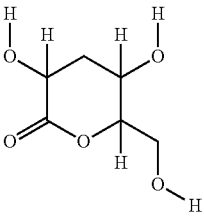 | OH source for $Fe_2O_3$ formation and Templating Agent |
| Cyclohexasiloxane, dodecamethyl-/14.84, 22.76 | 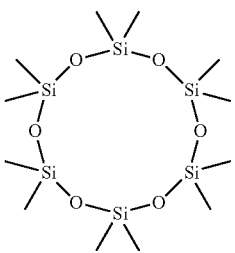 | |
| cyclohexylmethyl hexadecyl ester/18.3 | 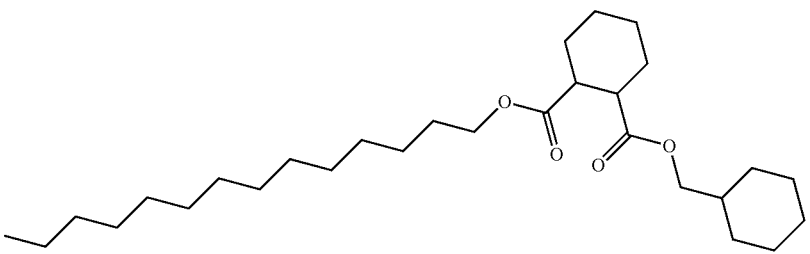 [SMILES: CCCCCCCCCCCCCCOC(=O)C1CCCCC1C(=O)OCC1CCCCC1] | |
| Sucrose/19.06 | 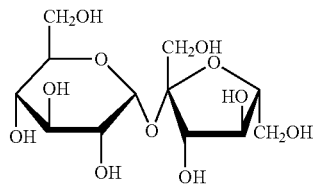 | Templating Agent |

TABLE 1-continued

Chemical compounds in the FSE as obtained from GC-MS measurements.

| Compound Name/<br>Retention Time (min) | Detailed Information | Function |
|---|---|---|
| Cyclononasiloxane,<br>octadecamethyl-/25.5,<br>26.76,28.22 | *(cyclic siloxane structure)* | |
| Cyclooctasiloxane,<br>hexadecamethyl-/19.35,<br>24.2 | *(cyclic siloxane structure)* | |

Analysis of Prepared Nanomaterials

Figure 4:
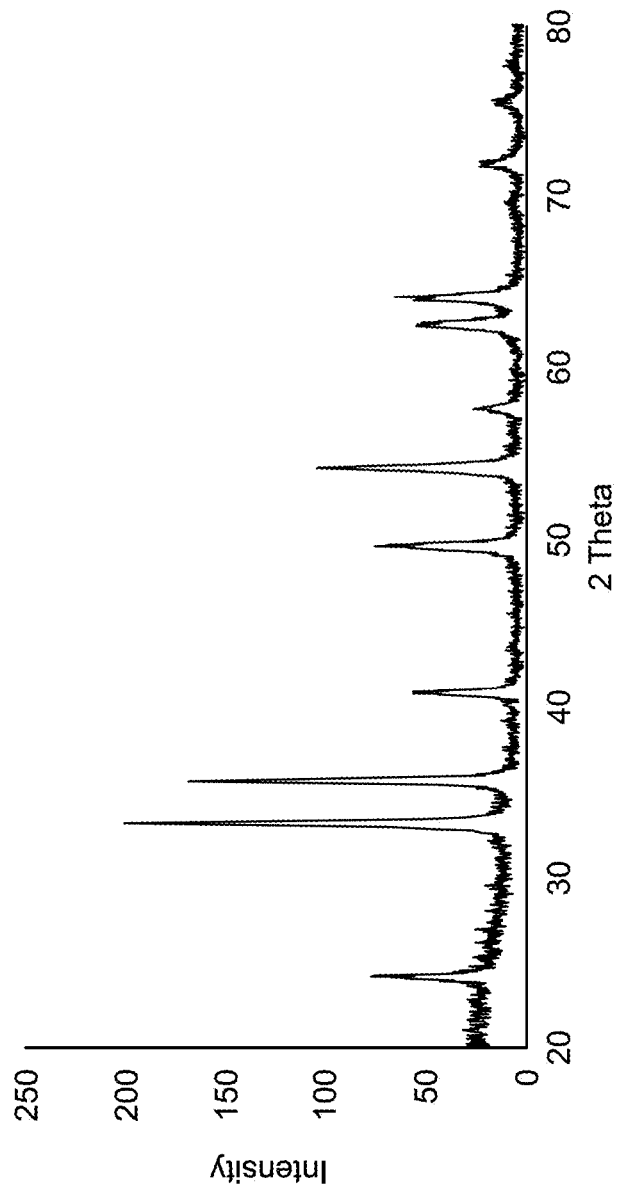
FIG. 4 shows the XRD pattern of the as-synthesized eco-friendly $\alpha$-$Fe_2O_3$.

The XRD pattern of $\alpha$-$Fe_2O_3$ is shown in FIG. 4. The XRD pattern of $\alpha$-$Fe_2O_3$ shows diffraction peaks at 24.13°, 33.15°, 35.612°, 40.85°, 49.48°, 54.09°, 57.59°, 62.41° and 63.99° which are indexed to the (012), (104), (110), (113), (024), (116), (018), (214) and (300) for rhombohedral $\alpha$-$Fe_2O_3$. The XRD results revealed the formation of pure and crystalline $\alpha$-$Fe_2O_3$, which agrees with the reported values (JCPDS Card No. 24-0072) [Rahman, et. al., Mater. Chem. Phys. J. Mater. Chem. A, 1, (2013), 5554-5561—incorporated here by reference].

The morphological features of the prepared $Fe_2O_3$ were investigated by SEM and TEM. The $Fe_2O_3$ particles were submerged and formed different shaped compound particles (FIGS. 5C & 5D). Interestingly, SEM image (FIG. 5C) shows the homogeneous spherical shaped particles of $\alpha$-$Fe_2O_3$ for the sample prepared with FSE. The diameter range of these spherical particles is between 100-300 nm. TEM images of $Fe_2O_3$ nanoparticles that were prepared in the presence or absence of FSE are shown in FIG. 6. Nanospheres or nanoballs of $\alpha$-$Fe_2O_3$ with size ranging from 100 to 300 nm are observed for the sample prepared in the presence of FSE, while irregular large-sized compound particles were obtained for the sample prepared by a chemical method in the absence of FSE.

Figure 7:
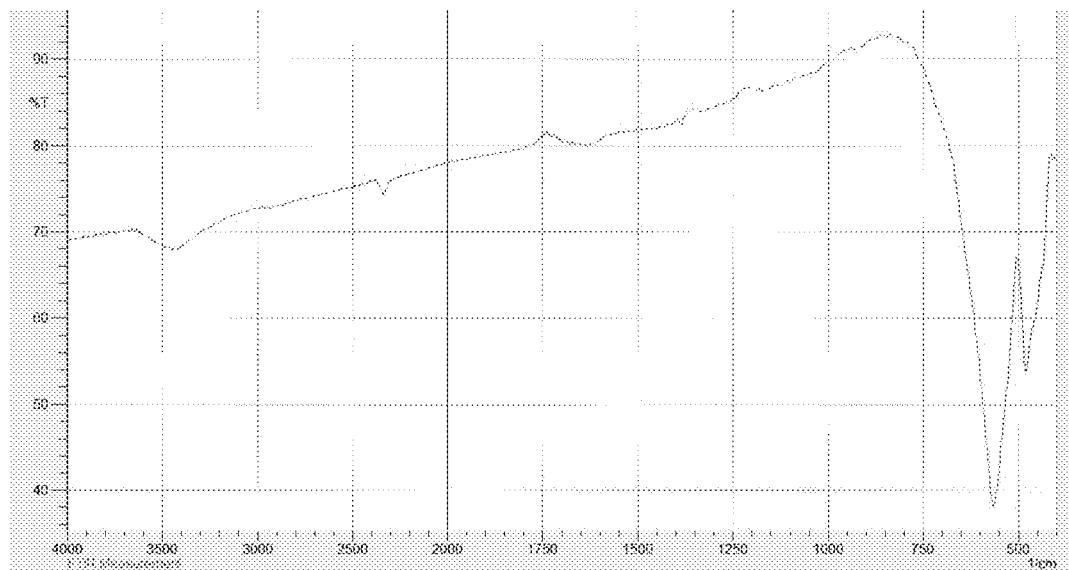
FIG. 7 is the FTIR spectrum of the as-synthesized eco-friendly the eco-friendly $\alpha$-$Fe_2O_3$.

The FTIR spectrum of $\alpha$-$Fe_2O_3$ spheres shows peaks at 550 and 470 $cm^{-1}$ which are attributed to the Fe—O bond vibration [Krehula, et. al., J. Alloys Compd., 431, (2007), 56-64-incorporated here by reference]. The peaks at 1625 and 3470 $cm^{-1}$ can be attributed to the asymmetrical and symmetrical stretching vibration of —OH group (FIG. 7B) [Rahman, et. al., Mater. Chem. Phys. J. Mater. Chem. A, 1, (2013), 5554-5561—incorporated here by reference].

Figure 8A:
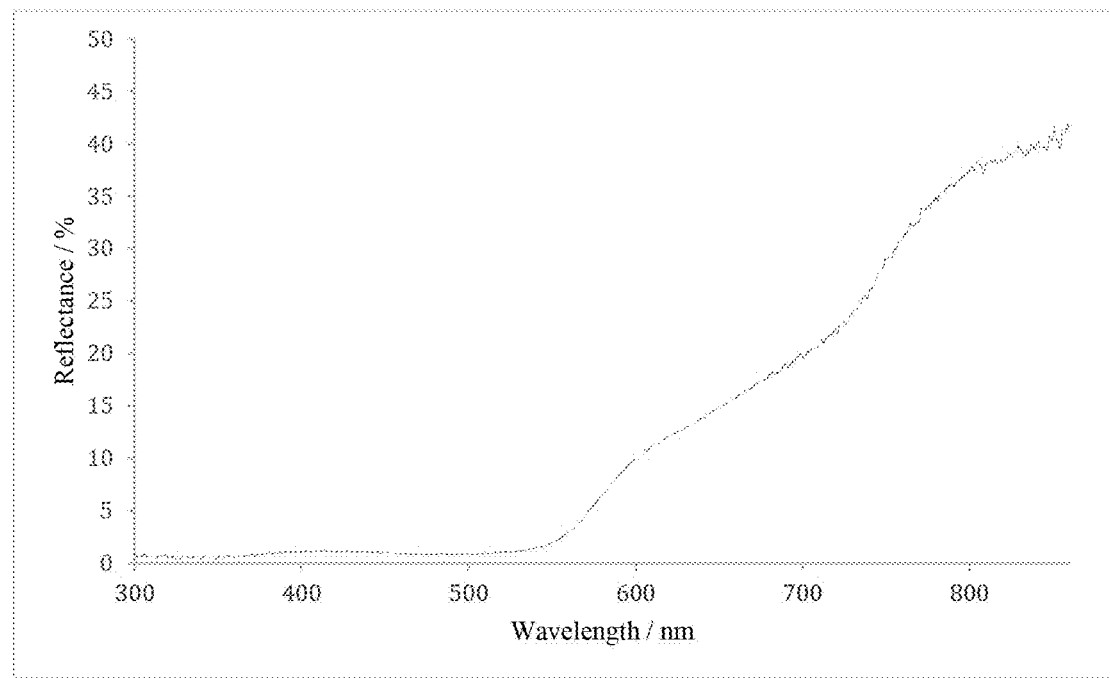
FIG. 8A is the UV-VIS diffuse reflectance spectrum of the eco-friendly $\alpha$-$Fe_2O_3$ prepared in the presence of LSE.
Figure 8B:
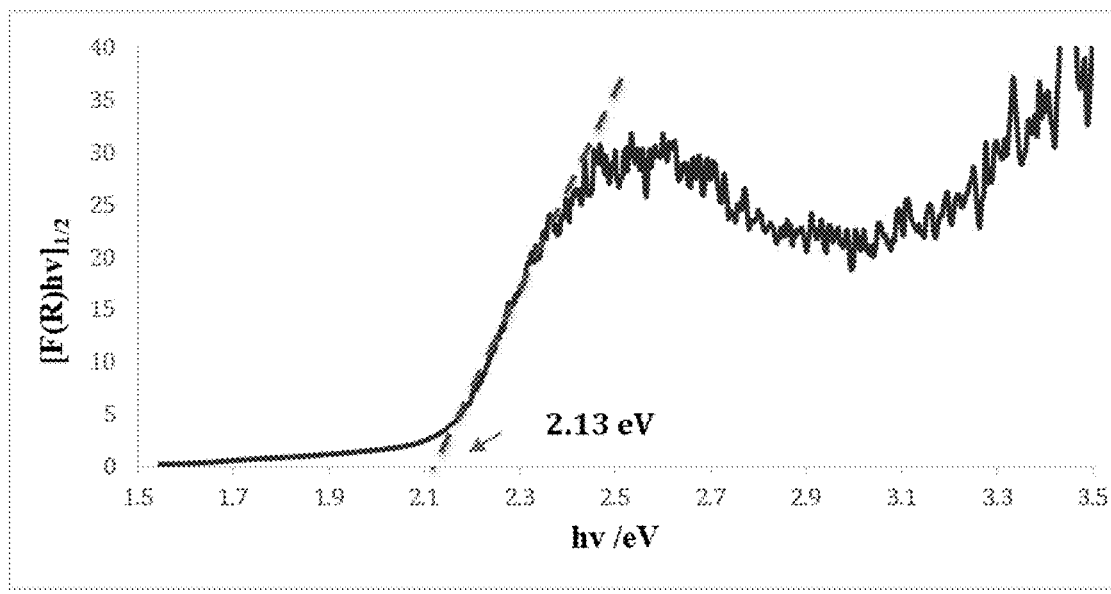
FIG. 8B is the Kubelka-Munk plot corresponding to the diffuse reflectance plot of FIG. 8A.

According to UV-vis Diffuse Reflectance measurements (FIG. 8A), $Fe_2O_3$ shows high absorption in the visible region with absorption edge of about 580 nm. For band gap calculations, the reflectance spectra of all samples were analyzed using the Kubelka-Munk relation to convert the reflectance into a Kubelka-Munk function. The band gab energy of all samples has been estimated roughly from the intercept of the tangents of Kubelka-Munk plots (see FIG. 8B). The obtained band gap energy of the green synthesized $Fe_2O_3$ (2.13 eV) is found to be in good agreement with the reported values.

Figure 9:
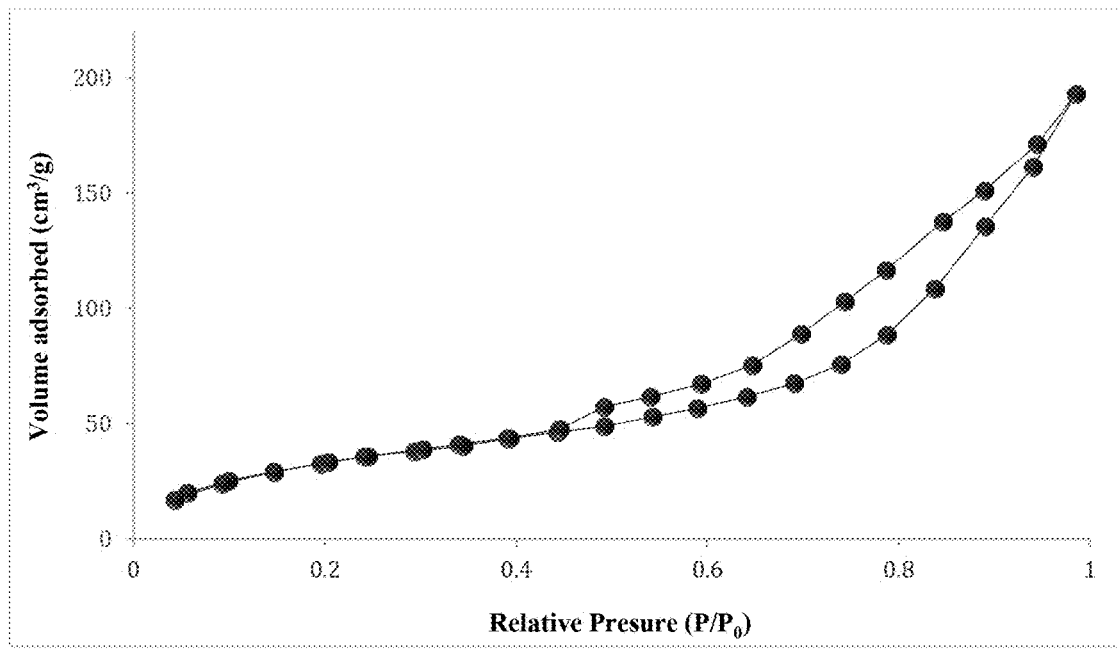
FIG. 9 is the $N_2$ adsorption-desorption isotherm of the as-synthesized eco-friendly $\alpha$-$Fe_2O_3$ prepared in the presence of LSE.

$N_2$ adsorption-desorption measurements were performed to determine the porosity of the samples (FIG. 9). The adsorption/desorption isotherms of $Fe_2O_3$ sample can be assigned to typical H3 hysteresis loop and reveal wide pore size distribution evidencing the uniform and non-accumulated particles. Eco-friendly $Fe_2O_3$ sample reveal large surface area of about 245.14 $m^2/g$. BET surface area, pore volume, and mean pore size data for both Eco-friendly $Fe_2O_3$ and chemically prepared $Fe_2O_3$ is presented in Table 2.

TABLE 2

The Surface area and the porous parameters of the as prepared nanomaterials.

| | BET ($m^2/g$) | Pore Volume (cc/g) | Pore size (nm) |
|---|---|---|---|
| Chemically prepared $Fe_2O_3$ | 112.24 | $1.37 \times 10^{-2}$ | 1.76 |
| Green $Fe_2O_3$ | 245.14 | $9.98 \times 10^{-2}$ | 8.24 |

Photocatalytic and Antibacterial Activity

Figure 10A:
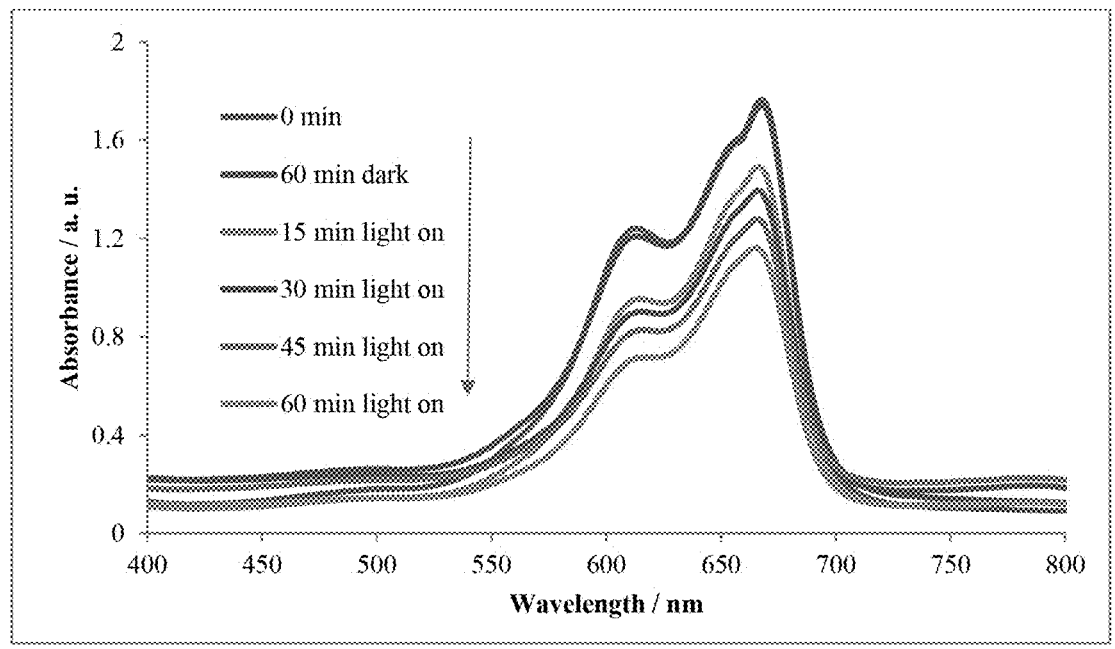
FIG. 10A is the UV-VIS adsorption spectrum of an aqueous solution of methylene blue during illumination in the presence of the $\alpha$-$Fe_2O_3$ prepared by chemical methods in the absence of LSE.
Figure 10B:
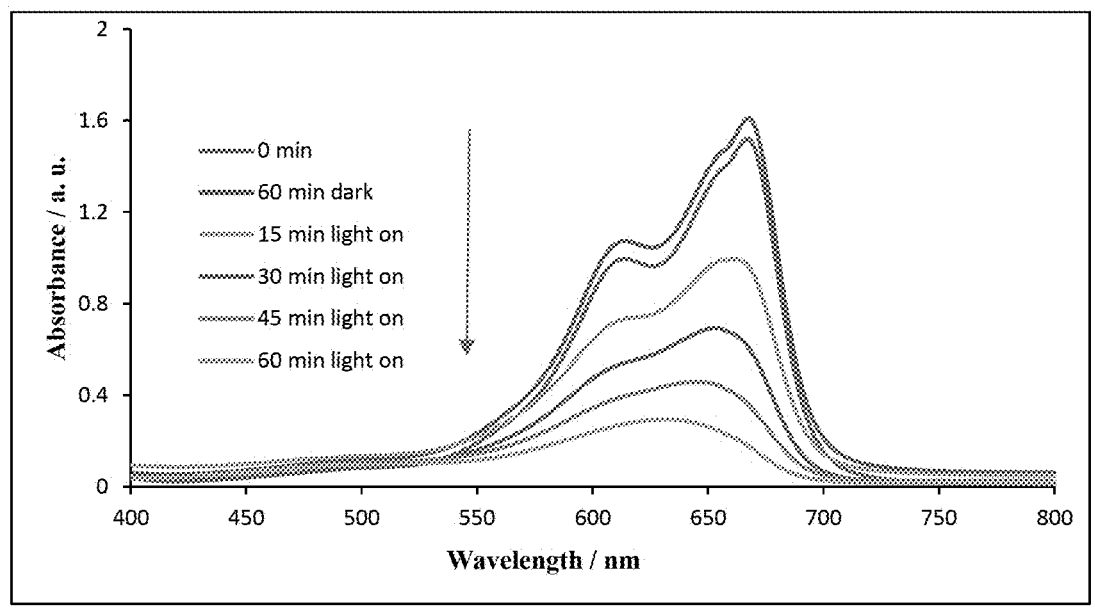
FIG. 10B is the UV-VIS adsorption spectrum of an aqueous solution of methylene blue during illumination in the presence of eco-friendly $\alpha$-$Fe_2O_3$ prepared in the presence of LSE.

Photocatalytic performance of the eco-friendly prepared $\alpha$-$Fe_2O_3$ nanomaterial was examined for the degradation MB dye under visible light irradiation. The concentration of the dye was monitored by spectrophotometric measurements. With the increase of visible light illumination time, the absorption peak assigned to MB at 668 nm decreases gradually (FIGS. 10A and 10B). MB dye alone did not exhibit any noticeable degradation under visible light. More efficient degradation has been achieved in presence of chemically $\alpha$-$Fe_2O_3$, resulting in the degradation of about 32% of MB dye in 60 min, while 86% of MB dye had been degraded in the presence of eco-friendly prepared $\alpha$-Fe$_2$O$_3$ nanospheres. Based on the above findings, the enhancement of the visible light photocatalytic activity of $\alpha$-Fe$_2$O$_3$ nanospheres can be attributed to increasing the surface area of green $\alpha$-Fe$_2$O$_3$ nanospheres compared to chemically prepared irregular $\alpha$-Fe$_2$O$_3$ nanoparticles, leading to increasing the amount of the adsorbed organic compounds for consequence degradation.

Figure 10C:
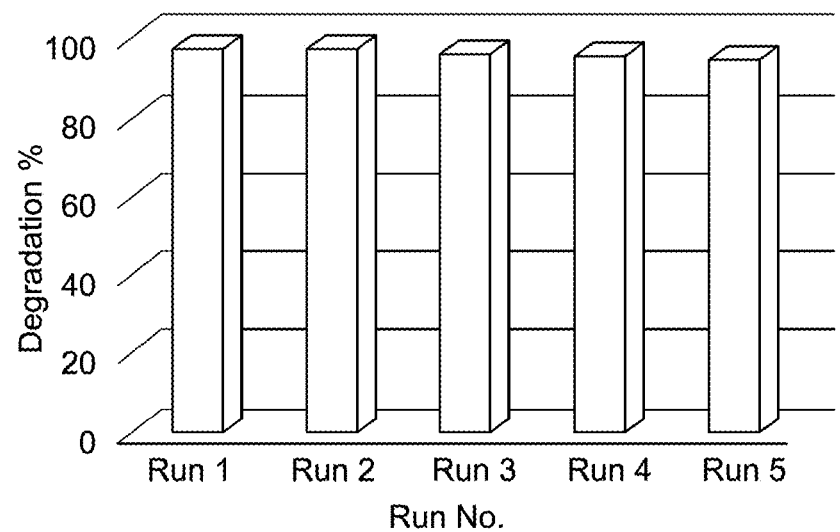
FIG. 10C is the recyclability of the eco-friendly $\alpha$-$Fe_2O_3$ prepared in the presence of LSE in the photocatalytic degradation of methylene blue.

The recyclability of the $\alpha$-Fe$_2$O$_3$ nanocomposite has been studied for 5 cycles of photocatalytic degradation of MB (20 mg $L$-1). It was found that, $\alpha$-Fe$_2$O$_3$ nanospheres can be used as stable and recyclable catalyst under visible light irradiation (FIG. 10C).

Figure 11A:
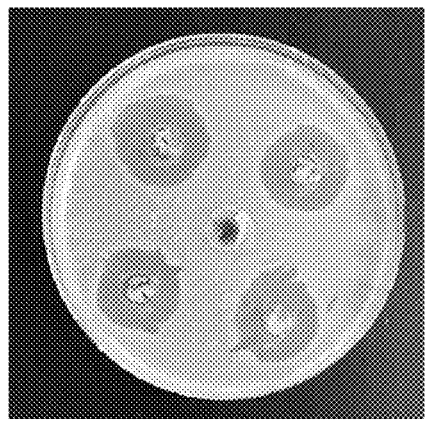
FIG. 11A is a photograph of a semi-solid agar plate with eco-friendly $\alpha$-$Fe_2O_3$ prepared in the presence of LSE showing antibacterial activity against *Staphylococcus aureus*.
Figure 11B:
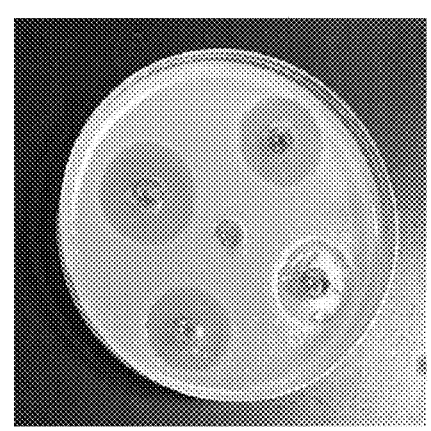
FIG. 11B is a photograph of a semi-solid agar plate with eco-friendly $\alpha$-$Fe_2O_3$ prepared in the presence of LSE showing antibacterial activity against *E. Coli*.
Figure 12:
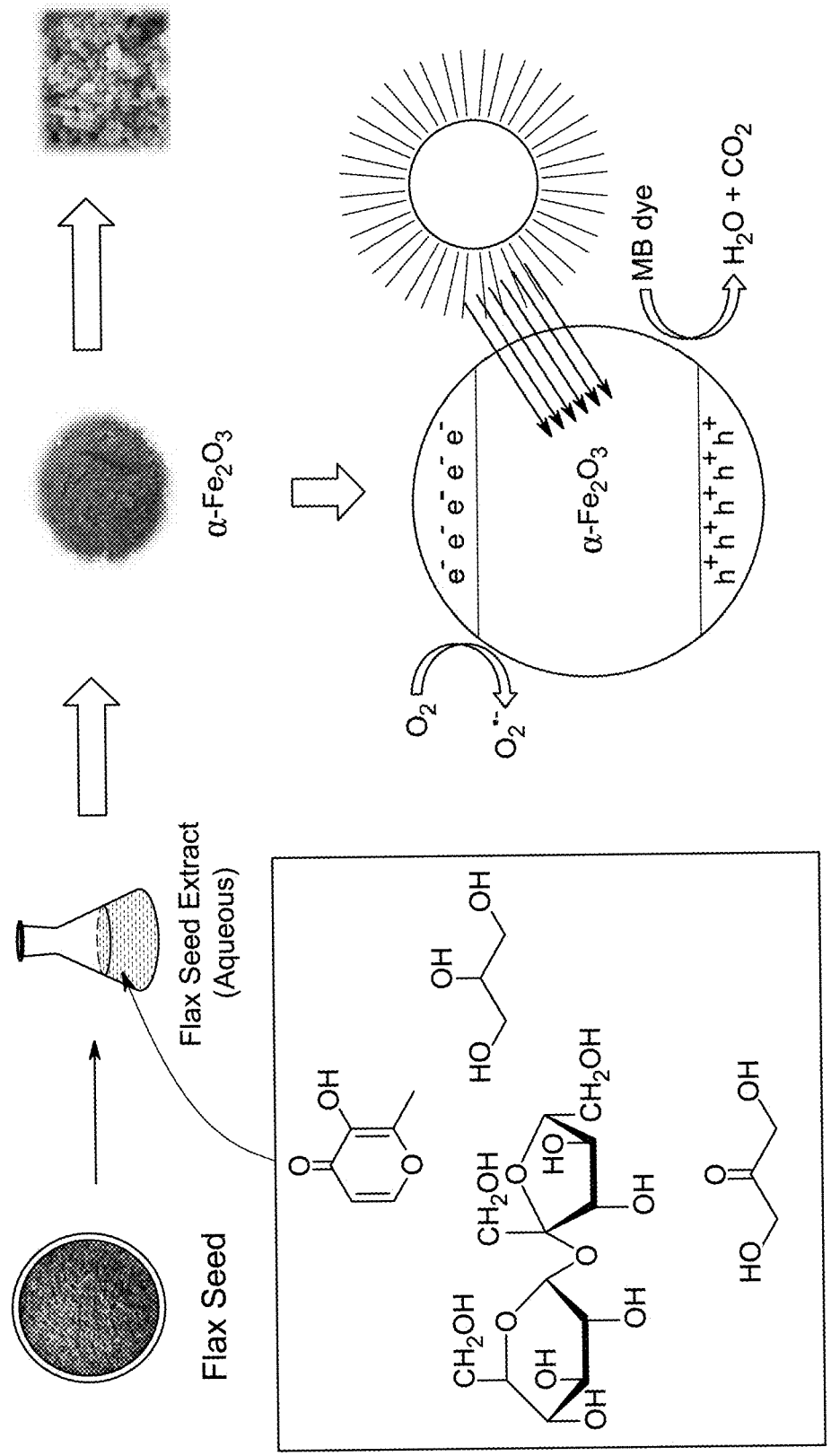
FIG. 12 is a schematic illustration of the proposed mechanism of the photocatalytic degradation of methylene blue on the eco-friendly $\alpha$-$Fe_2O_3$ prepared in the presence of LSE.

In addition, the green hematite nanospheres show high antibacterial activity against Gram positive and Gram Negative bacteria (FIGS. 11A & 11B). For bacterial growth, a lawn of culture was prepared by spreading the 100 mL of each test organism on nutrient agar plates. Plates were left standing for 10 minutes to let the culture get absorbed. Then 8 mm wells were punched into the nutrient agar plates for testing nanomaterial antimicrobial activity. Using a micropipette, 100 μL (50 μg) of the sample of nanoparticle suspension was poured onto each of five wells on all plates. After 24 hr incubation at 37° C.±2° C., the diameter of inhibition zone was measured. Antibiotic tetracycline (15 μg/wells) was used as a positive control. fresh culture having 106 colony-forming units (CFU)/mL The MIC was determined in Müller-Hinton broth using serial two-fold dilutions of nanoparticles in concentrations ranging from 10-200 μg/mL with adjusted bacterial concentration (0.10 at 625 nm (1×108 CFU/ml, 0.5 McFarland's standard). The MIC was noted by the visual turbidity of the tubes both before and after incubation and the experiments were carried out in triplicate, and averages were reported. The MBC was observed for presence or absence of bacterial growth in agar plates both before and after incubation. The data is presented in Tables 3 and 4 below.

TABLE 3

Data for the zone of inhibition of the $\alpha$-Fe$_2$O$_3$ nanoparticles compared to a standard small-molecule antibiotic.

| | Inhibitions zones diameters (mm) | |
|---|---|---|
| | $\alpha$-Fe$_2$O$_3$ nanoparticles | Tetracycline |
| E. coli | 35 ± 0.5 | 20 ± 0.2 |
| S. aureus ATCC 25923 | 24 ± 0.2 | 18 ± 0.2 |

TABLE 4

Data for the minimum inhibitory concentration and minimum bactericidal concentration of the $\alpha$-Fe$_2$O$_3$ nanoparticles.

| Bacterial strain | MIC(μg/mL) | MBC(μg/mL) |
|---|---|---|
| Staphylococcus aureus ATCC 25923 | 50 | 100 |
| E. coli | 7.25 | 12.5 |

The invention claimed is:

1. A method for the photodegradation of an organic pollutant comprising:
   mixing crystalline nanoparticles of $\alpha$-Fe$_2$O$_3$ with a treatment solution containing at least one organic pollutant selected from the group consisting of a dye, a phenol, and a polycyclic aromatic hydrocarbon, and a solvent to form a treatment composition; and
   irradiating the treatment composition with visible light to photodegrade the organic pollutant and form an exposed composition; then
   separating a solid product containing the crystalline nanoparticles of $\alpha$-Fe$_2$O, from the exposed composition and form a purified solution;
   wherein the crystalline nanoparticles of $\alpha$-Fe$_2$O; are spherical with a diameter from 50 to 500 nm and have an average sphericity of greater than 0.94 or a cross-section or projection with an average circularity of greater than 0.94;
   wherein the crystalline nanoparticles of $\alpha$-Fe$_2$O$_3$ have a band gap of 2.10 to 2.16 eV, a surface area of 240 to 260 m$^2$/g, a Type II BET nitrogen adsorption-desorption curve with a H3 hysteresis loop, and a mean pore size of 7.25 to 9.25 nm.

2. The method of claim 1, wherein the nanoparticles of $\alpha$-Fe$_2$O$_3$ are monodisperse, having a coefficient of variation defined as the ratio of a standard deviation of diameters to an average diameter of less than 0.15%.

3. The method of claim 1, wherein the nanoparticles of $\alpha$-Fe$_2$O$_3$ are present in the solution in an amount of 0.5 to 1.5 g/L.

4. The method of claim 1, further comprising:
   forming the crystalline nanoparticles of $\alpha$-Fe$_2$O$_3$ by:
      ultrasonically treating a nanoparticle synthesis solution comprising an iron (III)-containing precursor and a Linaceae seed extract derived from a seed from a plant in the family Linaceae to form a nanoparticle suspension; and
      recovering the crystalline $\alpha$-Fe$_2$O$_3$ nanoparticles from the nanoparticle suspension.

5. The method of claim 4, further comprising:
   forming the Linaceae seed extract by:
      boiling or steeping powdered seeds from the plant in the family Linaceae in water to produce a seed extract suspension; and
      filtering or otherwise removing solid particles from the seed extract suspension to produce the Linaceae seed extract.

6. The method of claim 5, wherein the Linaceae seed extract comprises:
   at least 4 of compounds selected from the group consisting of dihydroxyacetone, 2,2'-oxybisethanol, glycerin, 2-hydroxy-gamma-butyrolactone, maltol, and 3-deoxy-d-mannoic lactone; and either cyclohexylmethyl hexadecyl ester or sucrose.

7. The method of claim 4, wherein the iron (III)-containing precursor used to make the crystalline nanoparticles is iron (III) nitrate.

8. The method of claim 4, comprising:
   sonicating the nanoparticle synthesis solution at 45 kHz and 30 to 90 W.

* * * * *